United States Patent
Katz

(10) Patent No.: US 11,577,062 B2
(45) Date of Patent: Feb. 14, 2023

(54) SYSTEMS AND METHODS FOR IN-SITU, BOTTOM-UP TISSUE GENERATION

(71) Applicant: University of Florida Research Foundation, Inc., Gainesville, FL (US)

(72) Inventor: Adam J. Katz, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 628 days.

(21) Appl. No.: 16/604,900

(22) PCT Filed: Apr. 10, 2018

(86) PCT No.: PCT/US2018/026911
§ 371 (c)(1),
(2) Date: Oct. 11, 2019

(87) PCT Pub. No.: WO2018/191274
PCT Pub. Date: Oct. 18, 2018

(65) Prior Publication Data
US 2020/0376244 A1    Dec. 3, 2020

Related U.S. Application Data

(60) Provisional application No. 62/483,973, filed on Apr. 11, 2017.

(51) Int. Cl.
*A61M 37/00*    (2006.01)
*A61M 1/00*    (2006.01)
(Continued)

(52) U.S. Cl.
CPC ....... *A61M 37/00* (2013.01); *A61F 13/00068* (2013.01); *A61K 9/1658* (2013.01);
(Continued)

(58) Field of Classification Search
None
See application file for complete search history.

(56) References Cited

U.S. PATENT DOCUMENTS

| 2008/0241248 A1 | 10/2008 | France et al. |
| 2010/0098739 A1* | 4/2010 | Katz ............ C12N 5/0653 435/174 |

(Continued)

FOREIGN PATENT DOCUMENTS

| WO | 2016048243 A1 | 3/2016 |
| WO | 2016064902 A1 | 4/2016 |

OTHER PUBLICATIONS

International Search Report for PCT/US2018/026911 dated Jul. 3, 2018.

(Continued)

*Primary Examiner* — David W Berke-Schlessel
(74) *Attorney, Agent, or Firm* — Thomas Horstemeyer, LLP

(57) ABSTRACT

Embodiments of the present disclosure encompass systems and methods for in-situ/in vivo, bottom-up tissue generation for wound repair, repair of tissue defects, and the like. Embodiments of the systems of the present disclosure include modular scaffolds seeded with cells (modular tissue forming units (MTFUs)) for packing a tissue defect, such that these MTFUs are able to fill the wound bed with cells of one or more needed tissue types supported by the modular scaffolding particles.

20 Claims, 9 Drawing Sheets

(51) Int. Cl.
| | |
|---|---|
| A61L 27/36 | (2006.01) |
| A61L 27/38 | (2006.01) |
| A61F 13/00 | (2006.01) |
| A61L 27/54 | (2006.01) |
| A61K 9/16 | (2006.01) |
| A61K 35/28 | (2015.01) |

(52) U.S. Cl.
CPC ............ *A61K 9/1664* (2013.01); *A61K 35/28* (2013.01); *A61L 27/3608* (2013.01); *A61L 27/3834* (2013.01); *A61L 27/54* (2013.01); *A61M 1/90* (2021.05); *A61M 2037/0007* (2013.01)

(56) References Cited

U.S. PATENT DOCUMENTS

| | | |
|---|---|---|
| 2010/0160874 A1 | 6/2010 | Robinson et al. |
| 2010/0249801 A1 | 9/2010 | Sengun |
| 2011/0212179 A1 | 9/2011 | Liu |
| 2012/0157750 A1* | 6/2012 | Robinson .............. A61M 1/915 604/290 |
| 2012/0271418 A1 | 10/2012 | Hollister et al. |
| 2013/0034898 A1 | 2/2013 | Berry et al. |
| 2014/0148782 A1 | 5/2014 | Odland et al. |

OTHER PUBLICATIONS

Vijayavenkataraman S., et al. "3D bioprinting of skin: a state-of-the-art review on modelling, materials, and processes," Biofabrication [online], Sep. 7, 2016. vol. 8, Issue 3, article 032001, 31 pp.
Nichol, J. W., et al. "Modular tissue engineering: engineering biological tissues from the bottom up," Soft Matter [online], 2009, vol. 5, Issue 7, pp. 1312-1319.
Dankers P. Y. W., et al. "Supramolecular biomaterials. A modular approach towards tissue engineering," Bulletin of the Chemical Society of Japan [online], 2007k, vol. 80, Issue 11, pp. 2047-2073.
Amos et al., "Human Adipose-Derived Stromal Cells Accelerate Diabetic Wound Healing: Impact of Cell Formulation and Delivery", Tissue Engineering: Part A, 2010, 16(5): 1595-1606.
Bandeiras, C., et al., "Influence of the scaffold geometry on the spatial and temporal evolution of the mechanical properties of tissue-engineered cartilage: insights from a mathematical model", Biomech. Model Mechanobiol., 2015, 14(5): 1057-1070.
Chung, C. A., et al., "Enhancement of cell growth in tissue-engineering constructs under direct perfusion: Modeling and simulation." Biotechnology and Bioengineering, 2007, 97(6): 1603-1616.
Coletti, F., et al., "Mathematical modeling of three-dimensional cell cultures in perfusion bioreactors." Ind. Eng. Chem. Res., 2006, 45(24): 8158-8169.
Cook, C. A., et al., "Oxygen delivery from hyperbarically loaded microtanks extends cell viability in anoxic environments," Biomaterials, 2015, 52: 376-384.
Davis, K. E., et al., "The fluid dynamics of simultaneous irrigation with negative pressue wound thereapy", International Wound Journal, 2016,13:469-474.
Frohlich, M., et al., "Bone grafts engineered from human adipose-derived stem cells in perfusion bioreactor culture", Tissue Eng.: Part A, 2010, 16(1): 179-189.
Fukumura, D., et al., "Paracrine regulation of angiogenesis and adipocyte differentiation during in vivo adipogenesis." Circ Res, 2003, 93(9): e88-97.
Galban, C. J., et al., "Analysis of cell growth kinetics and substrate diffusion in a polymer scaffold", Biotechnol. Bioeng., 1999, 65(2): 121-132.
Galban, C. J., et al., "Effects of spatial variation of cells and nutrient and product concentrations coupled with product inhibition on cell growth in a polymer scaffold", Biotechnol Bioeng , 1999, 64(6): 633-643.
Guyot, Y., et al, "A three-dimensional computational fluid dynamics model of shear stress distribution during neotissue growth in a perfusion bioreactor", Biotechnol Bioeng, 2015, 112(12): 2591.
Huang, C., et al., "Effect of negative pressure wound therapy on wound healing", Curr Probl Surg., 2014, 51(7): 301-331.
Jurgens, W. J., et al., "Rapid attachment of adipose stromal cells on resorbable polymeric scaffolds facilitates the one-step surgical procedure for cartilage and bone tissue engineering purposes", J. Orthop Res., 2011, 29(6): 853-860.
Kapur, S. K., et al., "Human adipose stem cells maintain proliferative, synthetic, and multopotential properties when suspension cultured as self-assembling spheroids", Biofabrication, 2012, 4(2): 1-28.
Rioja, A. Y., et al., "Endothelial sprouting and network formation in collagen- and fibrin-based modular microbeads", Acta Biomater., 2016, 29: 33-41.
Sacco, R., et al., "A multiphysics/multiscale 2D numerical simulation of scaffold-based cartilage regeneration under interstitial perfusion in a bioreactor", Biomech. Model Mechanobiol., 2011, 10(4): 577-589.
Sengers, B. G., et al., "An integrated finite-element approach to mechanics, transport and biosynthesis in tissue engineering " Journal of Biomechanical Engineering—Transactions of the ASME, 2004, 126(1): 82-91.
Wang, S., et al., "Effect of fluid flow on smooth muscle cells in a 3-dimensional collagen gel model", Arterioscler. Thromb. Vasc. Biol., 2000, 20(10): 2220-2225.

* cited by examiner

FIG. 1: Prior Art

SYSTEMS AND METHODS FOR IN-SITU, BOTTOM-UP TISSUE GENERATION

CROSS-REFERENCE TO RELATED APPLICATIONS

This application is the 35 U.S.C. § 371 national stage application of PCT Application No. PCT/US2018/026911, filed Apr. 10, 2018, where the PCT claims priority to, and the benefit of, U.S. provisional application entitled "SYSTEMS AND METHODS FOR IN-SITU, BOTTOM-UP TISSUE GENERATION" having Ser. No. 62/483,973, filed Apr. 11, 2017, both of which are herein incorporated by reference in their entireties.

STATEMENT REGARDING FEDERALLY SPONSORED RESEARCH OR DEVELOPMENT

This invention was made with government support under W81XWH-13-2-0052 awarded by the United States Army. The government has certain rights to the invention.

BACKGROUND

Complex traumatic and surgical wounds constitute substantial burdens to the health care system, including extensive costs associated with extended hospitalizations, and risks of infection, thrombosis and flap/graft loss. The current standard of care for complex wounds includes external fixation, serial debridement of soft tissue, and replacement/repair of the honey defect. The 'state-of-the-art' solution for re-establishing bony continuity is the use of vascularized bone, such as a free fibula flap. This, however, requires a 6-8 hour operation by a surgeon with microsurgical expertise and creates a significant 'donor site defect' and associated pain, convalescence, and risks of infection, non-union, and malunion, at both the treatment and donor site. New treatment options are needed that replace and/or regenerate missing and damaged tissues while minimizing donor site harvest/morbidity.

Orthopedic injuries are the most common type of injury associated with recent armed conflicts, causing the majority of front-line evacuations and the majority of long-term disabilities. Nearly 80% of all injuries during such conflicts were due to explosive mechanisms, such as IEDs, mortars, and rocket-propelled grenades. The extent of trauma caused by blast injuries tends to be significant, resulting in severe bony injuries associated with extensive soft tissue deficits. Effective treatment of bone fractures is highly dependent on the quality and extent of surrounding soft tissues, and fracture healing is compromised at skeletal sites with a reduced soft tissue envelope. In fact, the more severe the soft-tissue damage, the higher the rate of non-union. Injury to the soft tissues is now accepted by most treating surgeons as being the most important component of high-energy trauma to the bony skeleton, dictating both the management, as well as determining the successful treatment outcome of such injuries.

Regenerative medicine has the potential to revolutionize the clinical treatment of complex wounds, such as those discussed above, that result from trauma, as well as those other tissue defects resulting from congenital anomalies, disease, surgery, or other condition. Traditional, "top down" tissue replacement and regeneration strategies face various challenges, such as slow vascularization, diffusion limitations, low cell density, and non-uniform cell distribution, that limit the long term feasibility of such approaches. The primary limitation to progress results from an inability to provide clinically-relevant solutions that provide adequate oxygen supply to larger construct dimensions needed for human-sized defects. Without new strategies to overcome this bottleneck, the field is destined to stagnate, or even fail completely.

SUMMARY

Briefly described, the present disclosure provides systems and methods for bottom-up generation of tissue in a wound bed using modular tissue forming units and negative pressure wound therapy to regenerate tissue in-situ.

Embodiments of a tissue generation system of the present disclosure include a plurality of modular tissue forming units (MTFUs) including: a plurality of biocompatible scaffolding particles seeded with a plurality of exogenous cells capable of forming at least one tissue type needed to repair a tissue defect, where the cells are initially coupled to the scaffolding particles; a perfusion fluid delivery conduit adapted to deliver media to a tissue defect packed with the MTFUs; and a negative pressure wound therapy (NPWT) system including a negative pressure wound dressing (NPWD) coupled to a subatmospheric pressure (SAP) device such that when the NPWD is secured over the tissue defect packed with the MTFUs, the SAP device and NPWD function to pull media through void spaces between the MTFUs packed within the tissue defect to perfuse the cells in the MTFUs with the media.

Methods of in-situ tissue regeneration according to embodiments of the present disclosure include: providing a plurality of modular tissue forming units (MTFUs); packing a tissue defect with the plurality of MTFUs such that void spaces exist between the MTFUs; providing a perfusion fluid delivery conduit having one or more fluid delivery outlets in the packed tissue defect to deliver a fluid to the tissue defect; and applying a negative pressure wound therapy (NPWT) system to the packed tissue defect to direct flow of the fluids from the perfusion fluid delivery conduit through the void spaces between the MTFUs to exit via the NPWT system. In embodiments, the MTFUs include a plurality of biocompatible scaffolding particles seeded with a plurality of exogenous cells capable of forming at least one tissue type needed to repair a tissue defect. In embodiments of the methods, the NPWT system includes a negative pressure wound dressing (NPWD) adapted to be placed over the packed tissue defect, such that the NPWD seals the tissue defect, and coupled to a subatmospheric pressure (SAP) device, such that when the NPWD is secured over the tissue defect packed with the MTFUs, the SAP device and NPWD function to direct flow of the fluids from the perfusion fluid delivery conduit through the void spaces between the MTFUs to the NPWD.

Other systems, methods, features, and advantages of the present disclosure will be or become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure. Moreover, in the drawings, like reference numerals designate corresponding parts throughout the several views.

FIG. 2 also illustrates neo-vessels forming within the packed bed that will inosculate with capillary sprouts emerging from the defect edges.

FIG. 3B is a digital image of an actual model of the system, and FIG. 3A is a schematic illustration of the system. Both FIGS. 3A and 3B show the following system components: A) infusion (inflow) catheter(s); B) packed bed of modular scaffold; C) sponge foam of NPWT system; D) interface between packed bed and NPWT foam; E) negative pressure out-flow system that drives the direction and magnitude of fluid flow, as well as evacuates excess fluid.

FIG. 6D is a graph illustrating the seeding efficiency of culture expanded ASC's vs. freshly isolated SVF cells.

DESCRIPTION

Figure 1:
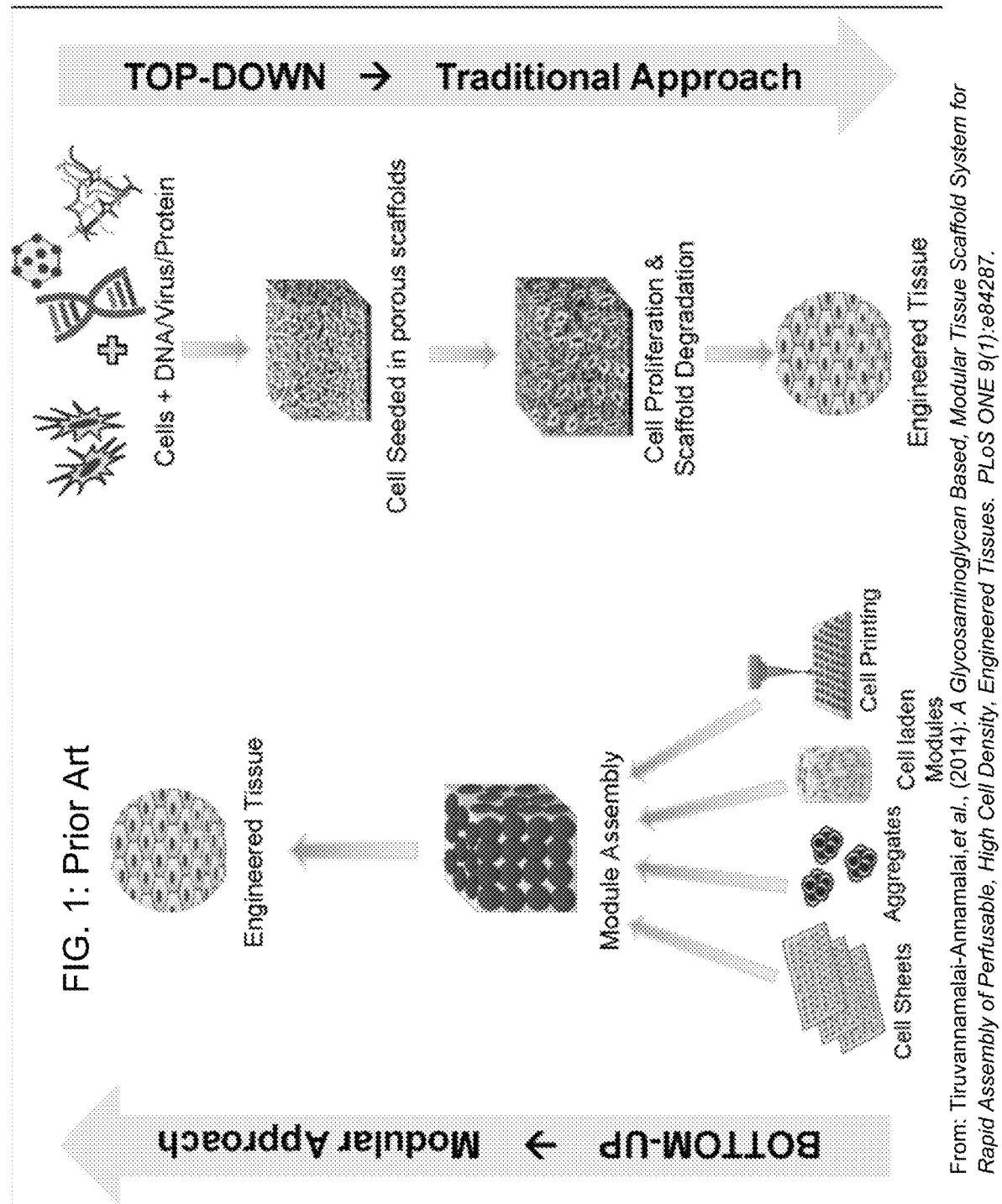
FIG. 1 shows schematic illustrations of top-down vs. bottom-up tissue replacement strategies. The traditional top-down approach (right) involves seeding cells into full sized porous scaffolds to form tissue constructs. This approach poses many limitations such as slow vascularization, diffusion limitations, low cell density and non-uniform cell distribution. In contrast, the modular or bottom-up approach (left) involves assembling small, non-diffusion limited, cell-laden modules to form larger structures and has the potential to eliminate the shortcomings of the traditional approach. From: Tiruvannamalai-Annamalai, Ramkumar; Randall Armant, David; W. T. Matthew, Howard (2014): *A Glycosaminoglycan Based, Modular Tissue Scaffold System for Rapid Assembly of Perfusable, High Cell Density, Engineered Tissues*. PLoS ONE 9(1):e84287, which is hereby incorporated by reference herein.

The details of some embodiments of the present disclosure are set forth in the description below. Other features, objects, and advantages of the present disclosure will be apparent to one of skill in the art upon examination of the following description, drawings, examples and claims. It is intended that all such additional systems, methods, features, and advantages be included within this description, be within the scope of the present disclosure, and be protected by the accompanying claims Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. Any such publications and patents that are intended to be incorporated by reference are specifically and individually indicated to be incorporated by reference as noted. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. Any terms not specifically defined within the instant application, including terms of art, are interpreted as would be understood by one of ordinary skill in the relevant art; thus, is not intended for any such terms to be defined by a lexicographical definition in any cited art, whether or not incorporated by reference herein, including but not limited to, published patents and patent applications. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, organic chemistry, biomedical engineering, medicine, computer modeling and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps. Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions:

In describing and claiming the disclosed subject matter, the following terminology will be used in accordance with the definitions set forth below.

As used in the present disclosure, the term "tissue defect" refers to open wounds and other injuries or defects in the tissue of the host, where the defect is capable of being filled or "packed" with modular tissue forming units of the present disclosure. In the discussion below, the terms "tissue defect" and "wound" may both be used, but neither is intended to be exclusive of the other.

As used herein the term "biocompatible" refers to the ability to co-exist with a living biological substance and/or biological system (e.g., a cell, cellular components, living tissue, organ, etc.) without exerting undue stress, toxicity, or adverse effects on the biological substance or system.

As used herein, the terms "biodegradable" and/or "bioabsorbable" refer to a material that, over time in a natural environment (e.g., within a living organism or living culture or in contact with cellular or tissue culture), dissolves, deteriorates, or otherwise degrades and loses its structure integrity and ceases to exist in its original structural form, without detriment to the host tissue(s). In embodiments of the present disclosure, biodegradable and/or bioabsorbable materials dissolve/degrade over a period of time within a host organism.

The terms "negative pressure" and "subatmospheric pressure" refer to a localized pressure that is lower than the pressure in the surrounding environment, such that the lower pressure is sufficient to create a pressure gradient to pull a fluid from the higher pressure environment to the area of localized lower pressure.

As used herein, "negative pressure wound therapy" or "NPWT" refers to a medical device or approach that employs negative pressure to/within a wound as part of the treatment/healing process. A NPWT system may include parts, such as a "negative pressure wound dressing" (NPWD) (e.g., a wound dressing adapted for use with negative pressure, which are known to those of skill in the art, and generally may include a foam component and/or wound cover pad), and/or a "subatmospheric pressure (SAP) device" (which may include, but is not limited to, a negative pressure device, and suction tubing coupled to the negative pressure device, and a fluid collection canister).

The term "modular tissue forming unit(s)" or "MTFU(s)" refers to a biocompatible, biodegradable particle (e.g., a small modular scaffolding unit) or plurality of such particles/modular units that are coupled to a plurality of exogenous cells. The cells of the MTFUs may be coupled within or on the particles. Although MTFUs refer to the modular scaffolding particles coupled to the cells, in some instances the term MTFU may also be used to refer to the modular particles prior to seeding with the cells, such as in an embodiment where a wound is packed with the modular scaffolding particles prior to seeding with cells (instead of embodiments where pre-seeded particles (MTFUs) are packed into the wound bed).

The terms "treat", "treating", and "treatment" are an approach for obtaining beneficial or desired clinical results. Specifically, beneficial or desired clinical results include, but are not limited to, alleviation of symptoms, diminishment of extent of disease, stabilization (e.g., not worsening) of disease, delaying or slowing of disease progression, substantially preventing spread of disease, amelioration or palliation of the disease state, and remission (partial or total) whether detectable or undetectable. In addition, "treat", "treating", and "treatment" can also be therapeutic in terms of a partial or complete cure for a disease and/or adverse effect attributable to the disease.

As used herein, the terms "prevent," "prophylactically treat," or "prophylactically treating" refer to completely, substantially, or partially preventing a disease/condition or one or more symptoms thereof in a host. Similarly, "delaying the onset of a condition" can also be included in "prophylactically treating", and refers to the act of increasing the time before the actual onset of a condition in a patient that is predisposed to the condition.

The term "host," "subject," or "patient" refers to any living entity in need of treatment, including humans, mammals (e.g., cats, dogs, horses, mice, rats, pigs, hogs, cows, and other cattle), birds (e.g., chickens), and other living species that are in need of treatment. In particular, the term "host" includes humans. As used herein, the term "human host" or "human subject" is generally used to refer to human hosts. Hosts that are "predisposed to" condition(s) can be defined as hosts that do not exhibit overt symptoms of one or more of these conditions but that are genetically, physiologically, or otherwise at risk of developing one or more of these conditions.

Description:

Embodiments of the present disclosure encompass systems and methods for in-situ/in vivo, bottom-up tissue generation for wound repair, repair of tissue defects, and the like. Embodiments of the systems of the present disclosure include modular scaffolds seeded with cells (modular tissue forming units (MTFUs)) for packing a tissue defect, such that these MTFUs are able to fill the wound bed with cells of one or more needed tissue types supported by the modular scaffolding particles. The modular nature of the MTFUs provides the ability to fill irregular wound structures including very small spaces or complicated geometries. In the present disclosure, the MTFUs are combined with a perfusion fluid supply vessel and conduits, and a negative pressure wound system to mediate flow of perfusion fluid through void space between the MTFUs within the tissue defect to assist the cells to grow and proliferate and form the needed tissues to repair the wound. The present disclosure also describes methods for using the systems of the present disclosure for in vivo, in-situ repair of tissue defects.

Generally speaking, tissue replacement and regeneration strategies fall into one of two categories, summarized in FIG. 1. Traditional "top-down" strategies involve seeding cells onto pre-fabricated scaffolds. Table 1, below, describes various challenges that limit each of these approaches.

fusion bioreactors, and clinically proven advanced wound care therapies, the present disclosure provides a novel translational approach to the challenge of matching neo-construct mass with nutrient demand/supply. In essence, the systems and methods of the present disclosure convert an open wound bed into a 'hybrid' packed bed perfusion bioreactor, leveraging advection and diffusion as a bridge to sustain cell viability while cell-laden "modules" organize into higher order 'neo-tissues' that ultimately integrate with surrounding host tissues. Although the paradigm can effectively address complex open wounds, this approach can also be modified and applied to 'internal' tissue/organ defects. For the purposes of illustration, in portions of the present disclosure, the systems and methods will be described below in the context of a complex open wound with segmental bone loss (e.g., of the tibia) and overlying soft tissue loss.

In embodiments, such complex open wounds will initially be treated using current standards of care, including placement of an external fixation device for stabilization of the proximal and distal bone fragments and maintenance of limb length. Serial debridement of soft tissue will also occur, as needed, to gain "control" of the wound prior to efforts to replace/repair the bone defect. Then, instead of the current 'state-of-the-art' approach involving complex reconstructive surgery techniques such as a free flap (e.g., fibula), with associated pain, risk of infection, and non-or mal-union of the donor-site tissue, with the methods and systems of the present disclosure the bone and tissue defect is repaired using an in-situ, bottom-up tissue regeneration/replacement approach.

Also, as discussed above, one of the critical factors for effective treatment of bone fractures, particularly those associated with extensive, surrounding, soft tissue deficits is the quality and extent of surrounding soft tissues. A reduced soft tissue envelope at fracture sites compromises the healing process and can increase the risk of non-union at these sites. The soft tissue envelope of bone is made of periosteum, muscle, fascia, subcutaneous adipose tissue and skin. Of these, periosteum is considered by many surgeons as the most critical component for normal and effective bone healing. Periosteum is a thin layer of fibrovascular tissue that covers essentially all bones in the body. It is made of a rich

TABLE 1

| Top-down Vascularization Strategies | |
|---|---|
| | Challenges |
| Cell-seeded macro-scaffolds Fabricated vascular beds | obtaining uniform cell seeding throughout scaffold delay (days-weeks) for vascularization to occur after implantation limited to very thin constructs (e.g. skin equivalents) exceptionally difficult to recapitulate the sophistication of a full microvascular/capillary bed with feeding arteriole and draining venule likely decades away would require technically demanding microvascular anastomoses (×2) for implantation of construct |
| Re-cellularization of de-cellularized tissues/organs | challenges with de-cellularization process challenges with re-cellularization process, especially achieving a non-thrombogenic, endothelial lined vessel bed requires surgical anastomoses for implantation requires a supply of donor organs/tissue which are in short supply |

Bottom-up strategies, on the other hand, reflect a motif found throughout nature and involve the directed or self-assembly of modular units that organize into more complex emergent systems. Using a therapeutic platform that applies and extends the principles of bottom-up self-assembly, permicrovascular network with associated endothelial cells and pericytes, as well as mesenchymal osteochrondrogenic progenitor cells. The systems and methods of the present disclosure provide an approach to (re)generate a fibrovascular tissue envelope akin to periosteum at a site of bony injury (e.g., in situ) using MTFUs including autologous cells coupled to modular scaffolding units and advanced wound care techniques.

Using the methods and systems disclosed in the present disclosure, negative pressure wound therapy is applied to a packed wound bed filled with modular, cell-seeded scaffolding units to generate flow and nutrient environments in the packed bed that are conducive to cellular survival and proliferation. The embodiment illustrated in FIG. 2, which will be described in greater detail below, illustrates the general principles of the methods and systems of the present disclosure. In the methods and systems of the present disclosure, a tissue defect is "packed" with an array of biocompatible modular scaffolds seeded with cells (hereafter 'modular tissue forming units', MTFUs) (represented by reference number 3 in FIG. 2). The scaffold material(s) and cell type(s) can be tailored to the specific clinical indication and tissue defect. In embodiments, the scaffolding materials are biodegradable or capable of being remodeled in vivo. Conceivably, any combination of biocompatible scaffold materials and cell types could be used that are compatible with the host and wound site being treated. In embodiments, MTFUs of the present disclosure for a single wound could include one or more types of scaffold materials/particles and/or one or more types of cells seeded to the scaffolding materials. In embodiments, the scaffolding particles are seeded with cells prior to packing in the tissue defect; however, it is also contemplated that in some embodiments the scaffolding particles can be packed into the tissue defect and seeded with cells after packing, e.g., via perfusion of the packed tissue defect with fluid (e.g., culture media) containing cells to be seeded.

In embodiments of the present disclosure. MTFUs are placed into the open tissue defect in an amount suitable to fill the majority of the space in the tissue defect, so as to achieve a pre-determined density. 3-D imaging can be used, as appropriate, to guide calculations of clinical defect volumes in advance. Methods for crude or detailed estimation of tissue volume are discussed in greater detail below. Due to the modular nature of the scaffold (for instance, the MTFUs can be various shapes/sizes, such as, but not limited to, spherical, string-like, irregular in shape, etc.), there will be void spaces in the packed bed between the MTFUs. For many shapes, such as spheres, the void space or "void fraction" relative to packed density has been mathematically determined for various packing styles (e.g., from thin, regular, cubic lattice-type packing; to loose random packing, to dense regular packing, and the like) (see, e.g., Dullien, F. A. L. (1992) Porous Media: Fluid Transport and Pore Structure ($2^{nd}$. Ed., Academic Press., hereby incorporated by reference herein).

After placement into the defect, the cells on and within the MTFUs are kept alive (in-situ/in-vivo) by diffusion of supportive nutrients from media/solutions that are perfused through the void space of the packed bed. The platform also allows for the use of any variety of culture media/solution(s) appropriate for the cell type, tissue type of interest, etc., and may be varied over time as determined by changing biological and/or clinical objectives. By altering the types and concentrations of additives, such as, but not limited to, growth factors, oxygen, inductive factors, anti-inflammatories, antimicrobials, or even additional cells within the perfusion fluid, the local wound bed and neo-construct milieu can be actively and dynamically influenced in vivo, much like traditional cell culture conditions/bioreactors. Additional details about the MTFUs and media are provided below.

In embodiments, the perfusion fluid (e.g., growth media) is supplied by a fluid delivery conduit (such as, but not limited to, medical tubing). It is, however, possible and within the scope of the present disclosure, that the perfusion fluid could be injected periodically thereby not requiring a separate perfusion delivery conduit. It is anticipated, however, that in most cases a tissue generation system of the present disclosure will include a perfusion delivery conduit. In embodiments the fluid delivery conduit is a modified surgical catheter(s). The perfusion fluid delivery conduit has one or more outlets for releasing/delivering the perfusion fluid to the packed wound bed/tissue defect. In embodiments, the delivery conduit has an outlet at or near the surface of the wound, and, due to the inflow rate of the fluid (e.g., via a pump), gravity, and/or the pressure gradient created by the NPWT device, the fluid is drawn into the tissue defect so as to 'saturate' the void space between the MTFUs within the packed bed, reaching even the deepest portions, and is drawn back up via the pressure gradient caused by the NPWT device, such as described in K. E. Davis, et al. (The fluid dynamics of simultaneous irrigation with negative pressure wound therapy; International Wound Journal, 2016; 13: 469-474, which is hereby incorporated by reference herein).

The supportive fluid/media may be continuously delivered and removed for constant and dynamic cycling of nutrients/waste; or the fluid may be delivered throughout the void space and allowed to 'dwell' without movement for a given time period before subsequent removal and replenishment with fresh media/nutrients. The rate of fluid exchange can be determined and altered based on specific objectives and/or empirically; or, may be guided by the levels of target analytes (e.g. glucose level; lactate) detected in fluid samples over time. In some embodiments, the perfusion delivery conduit (e.g., surgical catheter) may be placed percutaneously in a manner that locates one or more outlets deeper in the tissue defect, such as at the most dependent aspect of the wound. In embodiments, the perfusion delivery tubing is placed such that one or more outlets are located below/inferior to a substantial portion of the MTFUs (e.g., at the bottom of the packed bed/wound). In other embodiments the fluid delivery conduit includes one or more outlets at or near the surface of the packed tissue defect. In embodiments, the fluid delivery conduit includes outlets both at the surface of the packed tissue defect (e.g., superior to at least a portion of the MTFU's in the tissue defect) as well as one or more outlets below/inferior at least a portion of the MTFU's.

A modified negative pressure wound therapy (NPWT) dressing is placed over the opening of the tissue defect. In embodiments, the negative pressure wound dressing (NPWD) includes a foam material, such as, but not limited to an open-pore foam material. The NPWD can also include a covering, such as, but not limited to a semi-occlusive wound dressing. In embodiments the NPWD is sealed over the tissue defect. The NPWD is coupled (e.g., via an exit conduit, such as, but not limited to suction tubing, effluent tubing, etc.) to a subatmospheric pressure (SAP) device, such that subatmospheric pressure (SAP) will function to "pull" media through the void space of the packed bed of MTFUs. The NPWT system functions to remove fluid, assist wound contraction, protect and isolate the wound from the external environment, and positively influence angiogenesis, inflammation, and cellular proliferation and differentiation.

In embodiments, the NPVVT dressing can be coupled to a system/device, such as a vacuum pump or other device for inducing/enhancing/controlling the intensity of the negative/ subatmospheric pressure. In embodiments, the system can also include an evacuation conduit (e.g., tubing, reservoir, etc.) coupled to the NPVVT dressing and/or subatmospheric pressure device to evacuate excess 'waste' fluid, in a manner similar to removal of wound exudate by a traditional NPWT dressing from a draining wound. In embodiments, the evacuation conduit can be the same conduit as the perfusion delivery conduit. The SAP applied to the sealed foam mediates the flow of perfusion fluid (which can include, but is not limited to, nutrients, growth factors, etc.) through the void space of the packed bed of MTFUs, keeping cells alive by advection and diffusion and removing excess fluid and wound exudate. Advection/diffusion of fluids over cells is nature's mechanism for maintaining cell viability until definitive vascularization and tissue assembly, but is difficult to achieve in complex wound environments. Thus, the systems and methods of the present disclosure provide this flow of fluid and nutrients to create environments conducive to cell survival, growth and differentiation.

With the systems and methods of the present disclosure, over the course of time, cells within and upon the MTFUs in the packed wound bed will assemble into neo-vascular networks and lineage-induced micro-tissues that initially span each modular scaffold unit, and then coalesce with surrounding similar units. It is believed that the development of micro-tissue 'foci' will occur in synchrony with the development of neo-vessels and vice versa, as the intimate coupling of cell differentiation/histogenesis and vessel formation/angiogenesis is well described in the literature for many lineages, including muscle, nerve, bone and adipose (Fukumura, Ushiyama et al. 2003, Cao 2007, Jandial, Chen et al. 2011, Renault, Vandierdonck et al. 2013, Kusumbe, Ramasamy et al. 2014, Ramasamy, Kusumbe et al. 2014. Jabalee and Franz-Odendaal 2015, McClung, Reinardy et al. 2015, Duan, Wang et al. 2015, Shu, Xiao et al. 2016). Ultimately, the emerging neo-vascular network within the packed bed will connect with host microvasculature that is growing into the emerging construct from the surrounding wound edges, thereby mediating definitive host integration and healing. In embodiments, multiple, or other (e.g., different) layers of tissue (e.g. muscle, adipose) could be replaced in similar fashion, with sequential cycles of 'layered fabrication' using scaffold materials of strategic shapes along with lineage-directed cells chosen for a specific target tissue.

A biological premise underlying this strategic platform stems from the ability of MTFUs to assemble into an expanding network of neo-vessels that span between and amongst neighboring modular units, and ultimately inosculate with microvascular networks sprouting from the host wound bed itself. A technical challenge to re-building tissue in complex tissue defects is to dynamically support increasing volumes of MTFUs and growing tissue constructs via advection and diffusion until integration with host tissue occurs. The present disclosure provides systems, equipment, and methods that can provide this dynamic advection and diffusion support to the growing tissues in a scalable manner and can be applied in situ, directly on a patient's wound or tissue defect.

For purposes of illustration, Example 1, described in greater detail below, explores the variables and conditions that support microvessel network (MVN) formation in MTFU assemblies maintained in 2-dimensional in vitro static culture. Since vascularization is a limiting step to generating larger constructs, vasculogenesis is an important focus and outcome metric (along with cell proliferation and viability). Initial results presented in the examples below explore the role of ECM factors, cell concentration, and particle size on this process. Other variables can also be modulated with the systems and methods of the present disclosure, such as, but not limited to, scaffold size and material, pressure amplitude, and waveform (e.g. sine, square, continuous) to determine the effect on flow rate, shear stress, cell proliferation, apoptosis, ECM formation, mass transport and the generation of MVNs in perfused 3-D packed beds of MTFUs.

As mentioned above, the methods and systems of the present disclosure leverage the principles of NPVVI as a platform technology to generate bioreactor-like flow conditions for scalable vasculogenesis and histogenesis within a wound bed. Traditional NPWT typically involves the placement of an open-pore foam into a wound cavity, covered by a semi-occlusive wound dressing, and connected via suction tubing to a negative pressure device with a fluid collection canister. Over the last 15-20 years. NPWT has revolutionized the care of complex wounds and has become the standard-of-care for such. It functions to remove fluid, assist wound contraction, protect and isolate the wound from the external environment, and positively influences angiogenesis, inflammation, and cellular proliferation and differentiation through a number of mechanisms that are still being elucidated (Huang, Leavitt et al. 2014). In addition, the therapy is amenable to outpatient/ambulatory treatment paradigms. In the methods and systems of the present disclosure, subatmospheric pressure (SAP) is used to drive fluid movement through the void space of packed MTFUs to provide fresh supplies of nutrients to the seeded cells and growing tissues. Since NPWT systems currently in clinical use are not designed for mediating nutrient transport and could result in MTFU compaction with "no-flow" and/or increased fluid shear stresses, the systems and methods of the present disclosure employ modified NPWT components and devices for the purpose of optimizing in-situ mass transport through packed beds of MTFUs. In embodiments, operative flow can be determined and modified based on several parameters such as, but not limited to, the physical properties of the microcarrier particles, dimensions of the packed wound bed, the NPWT surface, the perfusion system, and boundary conditions. It is believed that the strategy of adapting NPWT approaches as a 'pump', or siphon for in vivo fluid perfusion and mass transport within a wound bed/tissue defect packed with exogenous materials (scaffolds and cells) from outside the body, has never been described and represents a new approach with the potential to revolutionize wound care, tissue repair/regeneration, and reconstructive surgery.

Figure 2:
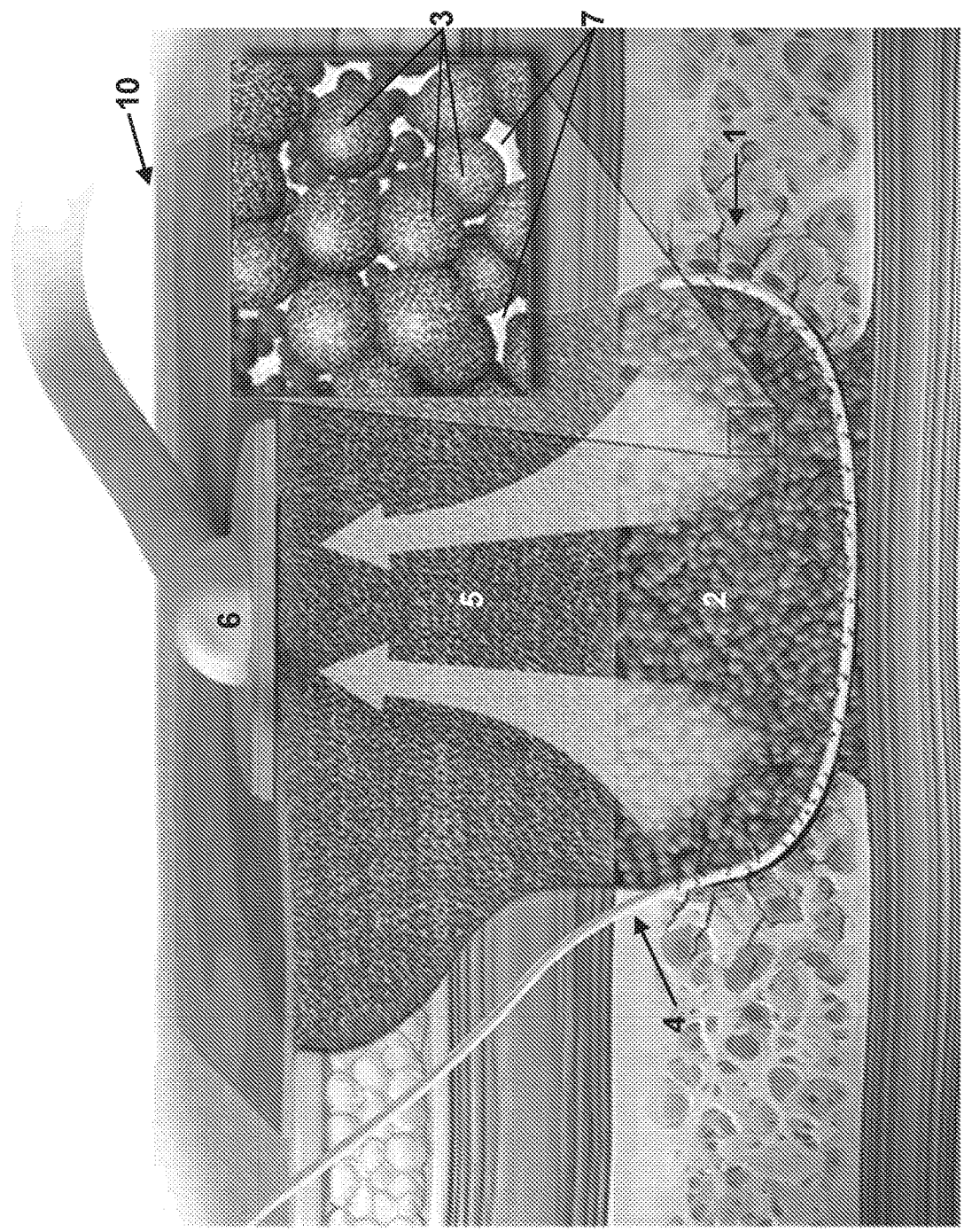
FIG. 2 illustrates an artistic rendering of an embodiment of a scalable system for in-situ, bottom-up tissue (re)generation according to the present disclosure. The defect involves segmental bone loss with overlying soft tissue defect. The figure illustrates a tissue defect (1), with the modular scaffolding (2) made of cell-seeded scaffolding particles (MTFUs) (3) (see call-out box). In this embodiment, a perfusion fluid delivery conduit (4) is placed via a remote percutaneous site for delivery of fluid and soluble factors. A NPWT system illustrated, includes a NPWD (5) placed on top of the wound and coupled to a SAP to mediate the flow of perfusion fluid through the void space of the packed bed of MTFUs, keeping cells alive by advection and diffusion.

Thus, in accordance with the principles outlined above, embodiments of systems of the present disclosure are described briefly below, with reference to FIG. 2, which illustrates elements of an embodiment of a tissue generation system (10) of the present disclosure in a tissue defect (1). As illustrated, embodiments of the system include a modular scaffolding material (2) that is made of a plurality of modular tissue forming units (MTFUs) (3) such as described above that include biocompatible scaffolding particles seeded with a plurality of exogenous cells of one or more tissue types needed to repair the tissue defect (1). The system also includes a perfusion fluid delivery conduit (4) adapted to deliver media to the tissue defect (1) packed with the MTFUs (3). In embodiments, the fluid delivery conduit may also be coupled to a fluid reservoir and/or a pump (not shown). The systems of the present disclosure also include a negative pressure wound therapy (NPWT) system, such as discussed above, including a negative pressure wound therapy dressing (NPWD) (5) coupled to a subatmospheric pressure (SAP) device (6). The NPWT systems is configured such that when the NPWD (5) (illustrated in FIG. 2 as an open-cell foam material with a top layer sealed over the wound) is secured over the tissue defect (1) packed with the MTFUs (3), the SAP device (6) and NPWD (5) function to create a pressure gradient to help pull media through void spaces (7) between the MTFUs (3) packed within the tissue defect to perfuse the cells in/on the MTFUs with the media. Subatmospheric pressure applied to the sealed foam mediates the flow of perfusion fluid through the void space of the packed bed of MTFUs, keeping cells alive by advection and diffusion. As neo-vessels form within the packed bed, they will inosculate with capillary sprouts emerging from the defect edges.

In embodiments, the MTFUs include a plurality of biocompatible and/or biodegradable scaffolding particles seeded with a plurality of cells. The MTFUs of the present disclosure are, as the name suggests, a group of independent modular units that are used together to pack into a tissue defect, such as an open wound site. The modular nature provides the ability to fit the geometry of complex wounds. The MTFUs for a single tissue defect can all be made of the same type of biocompatible scaffolding particles or different types. Similarly, the cells on the MTFUs can all be the same cell type or a combination of different cell types. Individual MTFUs can have a single cell type or multiple cell types, and MTFUs with different cell types can be combined to use in a single tissue defect. Multiple combinations of cell types and scaffolding particles can be made and used in the systems and methods of the present disclosure. The scaffolding particles of the MTFUs are biocompatible since they are designed for use in vivo. In embodiments, the scaffolding particles are also biodegradable/bioabsorbable or include a biodegradable material such that at least a portion of the MTFUs are biodegradable/bioabsorbable. In other embodiments, the MTFU's can be spheroids composed of self-assembling cells that generate their own extracellular matrix, such as described in Kapur et al., 2012 Biofabrication and Amos et al., 2010, Tissue Engineering (which are hereby incorporated by reference herein).

The scaffolding particles are small enough such that a tissue defect can be packed with a plurality of the MTFUs and such that multiple, small void spaces are present between individual MTFUs to allow the perfusion of fluid. In embodiments, the scaffolding particles are microparticles. The particles can have various shapes, such as, but not limited to, spherical, cord or string like, rod-like, irregular, or a combination of the above. In embodiments, the particles can range in size from about 10 microns to about 5 mm in diameter (or if elongated, such as a string or rod, similar diameters and unlimited length). In embodiments, the average diameter is about 25 to about 1000 microns. In embodiments, the average diameter is about 100 to 400 microns. The disclosure is also intended to include any intervening ranges. Additionally, the particles can have a solid consistency or they can have varying degrees of porosity depending upon the base material. They could also include highly porous electro-spun scaffolds with extensive void space and characterized by extensive interconnectivity.

The scaffolding particles can be made of any biocompatible, and optionally bioabsorbable material, such as gelatin, capable of being seeded with cells. Other potential scaffold/matrix materials can include, but are not limited to, collagens, laminins, fibrin, fibronectin, polycaprolactone, polyglycolide, polylactic acid, poly-3-hydroxybutyrate, and the like. In embodiments, the particles include an allogenic or autologous biological donor tissue material, such as bone. In embodiments, the scaffolding particles include cortical-cancellous (CC) bone particles and/or demineralized bone matrix (DBM) particles, or decellularized adipose or skin particles. Finally, the particles can also include diffusible oxygen (or other nutrients) incorporated within them (see e.g., Cook, Hahn et al, 2015).

The cells of the MTFUs are seeded on the scaffolding particles and, in embodiments, the cells are, at least initially, coupled to the scaffolding particles. In embodiments, the cells are exogenous cells capable of forming a tissue type needed to repair the tissue defect. In embodiments, the cells are human cells. In embodiments the cells can be allogenic cells, autologous cells, or a combination thereof. As used herein "exogenous" indicates that the cells seeded onto the scaffolding particles are provided from a source outside the wound and surrounding tissues, but the cells may be obtained from another part of the same host, e.g., "autologous". The cells can be coupled to the scaffolding particles via various methods, including coatings, specific or non-specific ligands, antibodies-antigen pairs, linkers, etc. The coupling can be a loose association (e.g., with cells adsorbed or absorbed within/on the particles or associated by non-covalent attachments). In other embodiments, more rigid attachments are used, such as covalent bonds via specific linker molecules or other methods known in the art. In embodiments the scaffolding particles are coated with serum before seeding with cells. The seeding density will depend on various factors such as the size of the scaffolding particles, size of the tissue defect, tissue-type, etc., but in embodiments a seeding density of about 1M cells/mg up to 1 million cells/mg of scaffold material could be possible.

In embodiments, at least a portion of the cells seeded onto/within the bioscaffolding particles are endothelial cells or cells capable of differentiating into endothelial cells in order to form vascular tissues. In embodiments, the cells are stem cells or progenitor cells. In embodiments the cells are a mixture of cell types capable of forming multiple tissue types. In embodiments, the cells are stem cells or other totipotent or pluripotent cells capable of differentiating into various cell types for forming different types of tissue. In embodiments the cells are adipose-derived cells, including but not limited to adipose derived stem cells (ADSCs) or adipose derived stromal vascular fraction (SVF) cells. Adipose-derived SVF cells are readily available in large numbers for autologous therapy, they are known to contain cell types involved in the formation of stable neo-vessels (including endothelial cells, endothelial progenitors, pericytes, and macrophages), and they are translatable to the clinical setting via 'point of care'/real-time use padigrams. SVF cells have the ability to spontaneously assemble into microvascular networks (MVNs).

In embodiments, the perfusion fluid delivery conduit is a biocompatible tubing material. It may also be biodegradable in full length, or partial length; drug-eluting (e.g., VEGF, HGF), nano-centimeter scale, conformable, with multiple configurations (e.g., tubes vs. 'soaker mat') and ideally modifiable in shape and dimensions by the applying person in real time. In embodiments, it is a modified surgical catheter. In embodiments, the perfusion fluid delivery conduit is coupled to a media reservoir to provide media for delivery to the tissue defect. The perfusion fluid delivery conduit can be placed directly in the tissue defect site, or it can be placed via a remote percutaneous site. In embodiments, the perfusion fluid delivery conduit is located such that it is at the "bottom" (inferior-most portion) of the tissue defect site (e.g., a portion furthest from the opening of the tissue defect, if an open wound situation), such that a substantial portion of the MTFUs are packed "above" or superior to (or "on top of") the delivery conduit outlet ports. In embodiments, the perfusion fluid delivery conduit includes multiple outlet ports through which media flows from the conduit into the tissue defect site. As discussed above, in embodiments one or more outlets may be located in an inferior location of the conduit and one or more outlets may be located more superficially (e.g., closer to the surface of the wound). However, in other embodiments, the perfusion delivery conduit can be located at a superior position of the wound closer to the surface, and may have an outlet located in the area near the interface of the wound and the wound dressing (e.g., the NPWD). It has been shown that even with a superior-located fluid delivery outlet, with the application of NPWT, fluid can be perfused throughout the tissue defects, without necessitating location of the delivery conduits at the lower portion of the tissue defect (see, K. E. Davis, et al., 2016, incorporated by reference above).

The perfusion fluid delivery conduit can also be coupled to a media reservoir to provide media for delivery to the tissue defect. The perfusion fluid can include a growth medium or combination of media and may include other components, such as growth factors, oxygen, blood, and the like. The perfusion fluid can be a standard or specialized growth medium, or may be customized to the tissue type/host. The perfusion delivery conduit and/or media reservoir may also be coupled to a pump to assist in fluid delivery to the tissue defect. In embodiments the negative pressure gradient induced by the NPVVT system is sufficient to drive fluid flow, but in some embodiments, fluid flow may be driven both by a SAP device of the NPWT system as well as by a pump coupled to the inflow system (perfusion fluid delivery conduit, media reservoir, etc.). Also, in embodiments, the perfusion delivery conduit can be the same conduit used to connect the NPVVT system and carry effluent out of the tissue defect, particularly if the perfusion is intermittent rather than continuous.

The NPWT system includes a NPWD adapted to be placed over the MTFU-packed tissue defect and coupled to a SAP device to drive a negative pressure gradient to direct the flow of perfusion fluid supplied by the perfusion fluid delivery conduit through the void spaces between the MTFUs to the NPWD. In embodiments the NPWD is a porous foam material and may also include a covering, such as a semi-occlusive or occlusive wound covering material. In embodiments the foam material is an open-celled foam. In embodiments the NPWD is adapted to be sealed over the tissue defect, such that it is a substantially air tight seal, effective to allow creation of the negative (e.g., subatmospheric) pressure. In embodiments, the SAP device includes a negative pressure source (such as, but not limited to, a vacuum pump) coupled to a negative pressure out-flow conduit. In embodiments, the negative pressure out-flow conduit is coupled to a waste collection reservoir for collecting exudate from tissue defect.

In embodiments the negative pressure source for the SAP device can be a simple vacuum pump or a more sophisticated vacuum pump programmable to generate fluid flows of different pressure gradients, flow rates, wave cycles, duration, and the like. Also, in embodiments, an outflow conduit of the NPWT system includes a waste reservoir that also includes monitors or outflow ports coupled to monitors for the evaluation of the components and parameters of the exudate, such as pH, glucose level, concentration of oxygen, carbon dioxide, lactic acid, and the like, which assist a caregiver in evaluating the status of the wound/tissue defect and the progress/status of tissue generation.

Although commercially available NPWT dressings could be used in the methods and systems of the present disclosure, traditional NPWT dressings may not be as effective or as well adapted for the uses of the present disclosure and could even result in detrimental shear stresses or scaffold contraction. Thus, in embodiments, the methods and systems of the present disclosure employ modified NPWD and NPWT systems. The modified dressings may be more rigid, or semi-rigid without a foam/sponge component; or the foam/sponge component may be of different material and/or porosity, biodegradable and/or drug eluting.

For internal defects (such as those without direct extension or exposure to the external environment; e.g., a segmental bone defect with adequate soft tissue coverage; or a mastectomy defect with overlying skin intact; or liver defect), different approaches are possible. One approach would be to use image guidance to generate 3-D printed tissue/organ 'templates' of the defect with borders composed of biocompatible/biodegradable material but with an otherwise open central cavity within which to pack MTFUs. These 3-D templates can include one or more inflow and outflow 'ports' with optimal size, number and position based on modeling. Another embodiment for internal defects can involve initial placement of an inert 'spacer' in the shape and size of the targeted tissue/organ (e.g., a silicone breast expander or implant for breast reconstruction; or placement of an antibiotic-loaded methylmethacrylate 'plug' for maintenance of space and delivery of antibiotics for a segmental bone defect). These inert materials may be left in place for 2-8 weeks to allow full encapsulation within the body. The fibrous capsule that forms serves to define a space, and after removal of the spacer, this space can be filled with MTFUs and irrigated as described previously for tissue repair/replacement. However, the application of SAP requires a 'venting' of the internal space. This can be achieved using rigid tube filled with porous sponge or similar material that extends from the packed bed space to the skin surface. The sponge is then sealed at the skin surface as described and connected to a SAP source.

For the vacuum source, it may involve different waveform and pressure amplitudes not currently available on existing systems. Finally, the entire system could include in-line monitors/sensors (e.g., for carbon dioxide, oxygen, glucose, pH, lactic acid, pressures, etc.) where the system may also include built-in pressure release valve(s) that provide real time feedback and alarms.

The fluid flow rate of the systems and methods of the present disclosure will depend on various factors related to the specific tissue defect to be treated, such as overall volume of the defect, size of the scaffolding particles, amount of void space, type of cells, and the like. A flow rate that is too high could generate a shear stress that could sweep away cells and/or nascent tissue growth. However, a flow rate that is too low may not stimulate sufficient cell differentiation or tissue growth.

In embodiments, intermittent perfusion is used, in which the void space of the packed tissue defect is estimated/calculated (e.g., via crude estimation or sophisticated computer modeling) (for instance, typically void spaces is from about 25-50% of the volume of the packed bed) and a volume of perfusion fluid equal to the estimated void space is perfused into the packed tissue defect and allowed to infiltrate and 'saturate' the entire void spaces and to "dwell" for an amount of time to allow for nutrient and waste exchange. After a dwell time ranging from about 30 min to 24 hours, the fluid is evacuated by engaging the SAP device of the NPVVT system to generate a negative pressure gradient to "pull" the exudate from the void spaces within the tissue defect out through the NPWD including an outflow conduit to a waste receptacle.

In other embodiments, continuous perfusion is used where the fluid is continuously delivered from perfusion delivery conduit into the tissue defect void space and out via the NPVVT system at a constant or varying flow rate. In embodiments, the void space of the packed tissue defect is estimated/calculated via estimation or sophisticated computer modeling/imaging to determine the volume of perfusion fluid to perfuse into the packed bed. For instance, if the packed bed has a volume of 100 ml and the estimated void space is approximately 40% (range of 25-50% of the packed bed) (see, e.g., Dullien 1992 incorporated above), the estimated void space volume would be about 40 ml. A continuous flow of 40-60 mls could be perfused over a given time period, such as 30 min to 24 hours. In embodiments, a continuous flow rate can be, but is not restricted to, about 1.5 to 5 ml/hr.

The present disclosure also includes embodiments of methods of using the in situ tissue generation systems of the present disclosure described above to generate/regenerate tissue in a tissue defect of a host. The methods will be described with reference to the systems and system components described above. Embodiments of the methods of in situ tissue regeneration of the present disclosure include providing a plurality of MTFUs, as described above, where the MTFUs include a plurality of biocompatible scaffolding particles seeded with a plurality of exogenous cells capable of forming at least one tissue type needed to repair the tissue defect.

The MTFUs are packed into the tissue defect. In embodiments, the MTFUs are packed sufficiently to fill the tissue defect and such that void spaces exist between the MTFUs. In embodiments, the void space is about 25-50% of the volume of the packed tissue defect. In embodiments, volume of the tissue defect for packing purposes can be estimated based on the known estimation methods (such as volume of fluid capable of filling the defect, etc.). In other embodiments, more sophisticated computer imaging and modeling can be employed, as described in more detail in the embodiments below, to optimize the packing efficiency of the MTFUs for the specific tissue defect site. In embodiments, computer modeling can also be used to determine optimal size and shape of the MTFUs for the specific tissue defect site.

The methods of the disclosure also include providing a perfusion fluid and, in embodiments, a perfusion delivery conduit having one or more fluid delivery outlets to deliver fluids to the tissue defect, the perfusion delivery drain/outlet located to provide fluid to the tissue defect. The methods of the present disclosure include applying a NPWT system to the packed tissue defect to direct flow of fluids from the perfusion fluid delivery conduit through the void spaces of the packed tissue defect, and out via the NPWT system.

In embodiments, the NPWT system includes a negative pressure wound dressing (NPWD) that is placed over the packed tissue defect, such that the NPWD seals the tissue defect. The NPWD is coupled to a SAP device such that when the NPWD is secured over the tissue defect packed with the MTFUs, the SAP device and NPWD function to create a negative pressure gradient to "pull" or direct flow of the fluids from the perfusion fluid delivery conduit through the void spaces between the MTFUs to the NPWD. In some embodiments, the system may also include positive pressure, such as from a mechanical or elastomeric pump, etc. that may be coupled to the perfusion fluid delivery conduit or reservoir. Thus, in embodiments, fluid flow is directed by a combination of a positive pressure from a pump and a negative pressure from the NPWT system. In embodiments, the SAP device includes a negative pressure source (such as, but not limited to a vacuum) coupled to a negative pressure out-flow conduit. In embodiments, the NPWD and SAP device form a NPWT system that may also include a waste collection reservoir coupled to the negative pressure outflow conduit to collect effluent from the tissue defect.

Methods of the present disclosure, in embodiments, also include, providing various fluids to flow through the system. In embodiments, the fluids can include media, such as growth media (including, but not limited to, various nutrients, growth factors, which, in embodiments, may be customized to the tissue type or the specific tissue defect). In embodiments, the perfusion fluids can also include oxygen, growth factors, blood, or other general or specialized growth-directing fluids.

In embodiments of the methods of the present disclosure, the MTFUs are custom-made to meet the needs of the specific tissue defect of interest. The scaffolding particles, cell types, and any other components of the MTFUs can be selected to optimize regeneration of the specific tissue type or types in the tissue defect. In embodiments, the perfusion fluid can also be customized to the patient or specific tissue defect, such as in selection of growth factors, base media, growth media, etc. In embodiments computer imaging and/or computer modeling is employed to determine the physical parameters of the tissue defect, the placement of the fluid conduit and/or the location of the fluid delivery outlets of the conduit within the tissue defect, and or the fluid flow rate, intensity of the negative pressure generation, and the like in order to tailor various aspects of the system/method to optimize tissue growth for the specific tissue defect.

Additional details regarding the methods and systems of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

Aspects

The following listing of exemplary aspects supports and is supported by the disclosure provided herein.

Aspect 1. A tissue generation system comprising: a plurality of modular tissue forming units (MTFUs) comprising: a plurality of biocompatible scaffolding particles seeded with a plurality of exogenous cells capable of forming at least one tissue type needed to repair a tissue defect, wherein the cells are initially coupled to the scaffolding particles; a perfusion fluid delivery conduit adapted to deliver media to a tissue defect packed with the MTFUs; and a negative pressure wound therapy (NPWT) system comprising a negative pressure wound dressing (NPWD) coupled to a subatmospheric pressure (SAP) device such that when the NPWD is secured over the tissue defect packed with the MTFUs, the SAP device and NPWD function to pull media through void spaces between the MTFUs packed within the tissue defect to perfuse the cells in the MTFUs with the media.

Aspect 2. The tissue generation system of aspect 1, wherein the biocompatible scaffolding particles are microparticles.

Aspect 3. The tissue generation system of aspect 1 or 2, wherein the biocompatible scaffolding particles have an average diameter of about 25 to 1000 μm.

Aspect 4. The tissue generation system of any of aspects 1-3, wherein the biocompatible scaffolding particles are selected from the group consisting of: cortical-cancellous (CC) bone particles, demineralized bone matrix (DBM) particles, and gelatin microspheres.

Aspect 5. The tissue generation system of any of aspects 1-4, wherein the biocompatible scaffolding particles are coated with serum before seeding with cells.

Aspect 6. The tissue generation system of any of aspects 1-5, wherein the biocompatible scaffolding particles are seeded with cells at a seeding density of about 100,000 to 10 million cells/mg.

Aspect 7. The tissue generation system of any of aspects 1-6, wherein the cells are human cells capable of differentiating into endothelial cells.

Aspect 8. The tissue generation system of any of aspects 1-7, wherein the cells are stem cells or progenitor cells.

Aspect 9. The tissue generation system of any of aspects 1-8, wherein the cells are adipose derived stem cells (ADSCs) or adipose derived stromal vascular fraction (SVF) cells.

Aspect 10. The tissue generation system of any of aspects 1-9, wherein the perfusion fluid comprises growth media.

Aspect 11. The tissue generation system of aspect 10, wherein the growth media comprises growth factors capable of stimulating growth of the at least one tissue type.

Aspect 12. The tissue generation system of any of aspects 1-11, wherein the perfusion fluid delivery conduit comprises a modified surgical catheter.

Aspect 13. The tissue generation system of any of aspects 1-12, further comprising a media reservoir coupled to the perfusion fluid delivery conduit to provide media for delivery to the tissue defect.

Aspect 14. The tissue generation system of aspect 13, further comprising a pump coupled to one or more of the media reservoir or the perfusion fluid delivery conduit to initiate flow of fluid from the media reservoir through the perfusion fluid delivery conduit to the tissue defect.

Aspect 15. The tissue generation system of any of aspects 1-14, wherein the NPWD comprises a porous foam material.

Aspect 16. The tissue generation system of any of aspects 1-15, wherein the SAP device comprises a negative pressure source coupled to an out-flow conduit.

Aspect 17. The tissue generation system of aspect 16, wherein the negative pressure source comprises a vacuum pump.

Aspect 18. The tissue generation system of any of aspects 1-17, wherein the NPWT system further comprises a waste collection reservoir coupled to the out-flow conduit to collect effluent from the tissue defect.

Aspect 19. The tissue generation system of any of aspects 1-18, wherein at least a portion of the cells differentiate into endothelial cells and form vessels among the scaffolding particles.

Aspect 20. A method of in-situ tissue regeneration, the method comprising: providing a plurality of modular tissue forming units (MTFUs), the MTFUs comprising: a plurality of biocompatible scaffolding particles seeded with a plurality of exogenous cells capable of forming at least one tissue type needed to repair a tissue defect; packing a tissue defect with the plurality of MTFUs such that void spaces exist between the MTFUs; providing a perfusion fluid delivery conduit having one or more fluid delivery outlets in the packed tissue defect to deliver a fluid to the tissue defect; and applying a negative pressure wound therapy (NPWT) system to the packed tissue defect, the NPWT system comprising a negative pressure wound dressing (NPWD) adapted to be placed over the packed tissue defect, such that the NPWD seals the tissue defect, and coupled to a subatmospheric pressure (SAP) device, such that when the NPWD is secured over the tissue defect packed with the MTFUs, the SAP device and NPWD function to direct flow of the fluids from the perfusion fluid delivery conduit through the void spaces between the MTFUs to the NPWD.

Aspect 21. The method of aspect 20, wherein the perfusion delivery conduit is placed such that at least one of the fluid delivery outlets is located inferior to at least a portion of the MTFUs.

Aspect 22. The method of aspect 20, wherein the perfusion delivery conduit is placed such that at least one of the fluid delivery outlets is located at the surface of the tissue defect, superior to at least a portion of the MTFUs.

Aspect 23. The method of any of aspects 20-22, wherein the biocompatible scaffolding particles are microparticles.

Aspect 24. The method of any of aspects 20-23, wherein the biocompatible scaffolding particles are selected from the group consisting of cortical-cancellous (CC) bone particles, demineralized bone matrix (DBM) particles, and gelatin microspheres.

Aspect 25. The method of any of aspects 20-24, further comprising, coating the biocompatible scaffolding particles with serum before seeding with cells.

Aspect 26. The method of any of aspects 20-25, wherein the cells are human cells capable of differentiating into endothelial cells.

Aspect 27. The method of any of aspects 20-26, wherein the cells are stem cells.

Aspect 28. The method of any of aspects 20-27, wherein the cells are adipose derived stem cells (ADSCs) or adipose derived stromal vascular fraction (SVF) cells.

Aspect 29. The method of any of aspects 20-28, wherein the perfusion fluid comprises growth media.

Aspect 30. The method of any of aspects 20-29, wherein the perfusion fluid delivery conduit comprises a modified surgical catheter.

Aspect 31. The method of any of aspects 20-30, wherein the perfusion fluid delivery conduit is coupled to a media reservoir to provide media for delivery to the tissue defect.

Aspect 32. The method of any of aspects 20-31, wherein the NPWD comprises a porous foam material.

Aspect 33. The method of any of aspects 20-32, wherein the SAP device comprises a negative pressure source coupled to a negative pressure out-flow conduit.

Aspect 34. The method of aspect 33, wherein the negative pressure source comprises a vacuum pump.

Aspect 35. The method of aspect 33 or 34, wherein the negative pressure out-flow conduit is coupled to a waste collection reservoir to collect effluent from the tissue defect.

Aspect 36. The method of any of aspects 20-35, wherein at least a portion of the cells differentiate into endothelial cells and form vessels among the scaffolding particles.

Aspect 37. The method of any of aspects 20-36, wherein the fluid is continuously perfused through the tissue defect.

Aspect 38. The method of aspect 37, wherein the flow rate is a function of a flow of the fluid from a pump coupled to the perfusion catheter and the subatmosphereic pressure generated by the SAP device and NPWD.

Aspect 39. The method of any of aspects 20-36, wherein the fluid is intermittently perfused through the tissue defect such that the tissue defect is infused with fluid, which is removed via the NPWT system after a time period of about 30 min to 24 hours.

Aspect 40. The method of any of aspects 20-39, further comprising, prior to packing the tissue defect with MTFUs, imaging the tissue defect with a 3D imaging device to produce 3D imaging data, calculating the volume and shape of the tissue defect based on the 3D imaging data; optimizing the placement of the perfusion fluid delivery conduit and the packing density of the MTFU's based on the calculated volume and shape of the tissue defect.

From the foregoing, it will be seen that aspects herein are well adapted to attain the ends and objectives hereinabove set forth together with other advantages which are obvious and which are inherent to the systems and methods.

It will be understood that certain features and subcombinations are of utility and may be employed without reference to other features and subcombinations. This is contemplated by and is within the scope of the aspects.

While specific elements and steps are discussed in connection to one another, it is understood that any element and/or steps provided herein is contemplated as being combinable with any other elements and/or steps regardless of explicit provision of the same while still being within the scope provided herein. Since many possible aspects may be made of the disclosure without departing from the scope thereof, it is to be understood that all matter herein set forth or shown in the accompanying drawings is to be interpreted as illustrative and not in a limiting sense.

EXAMPLES

Now having described the embodiments of the present disclosure, in general, the Examples below describe some additional embodiments of the present disclosure. While embodiments of the present disclosure are described in connection with the Examples and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

Use of Negative Pressure to Mediate Fluid Flow Through a Packed Bed Assembly of Microspheres The use of negative pressure to effect perfusion of fluid through a packed-bed bioreactor described in the present example. Using the customized packed-bed system shown in FIGS. 3A and 3B, the present example demonstrated the perfusion of fluid through the void space of a packed bed of modular micro-scaffolds using NPWT within a customized in-vitro system. The particles had a size range of about 50-250 μm, and the packed bed volume was approximately 7 ml.

Negative pressures were applied in a manner that directly modeled the clinical use of NPWT to effect the perfusion of fluid through the void space of packed beds of modular scaffolds (e.g., gelatin microspheres). Fluid was perfused at 50-75 mmHg. In order to quantify flow fields, computational transport models were developed in ANSYS CFD (ANSYS, Inc., Canonsburg, Pa.) for this bioreactor system. Fluid flow was generated by (i) pressure difference or (ii) constant volumetric flow rate prescribed at inlet and outlet openings. The system is shown in schematic in FIG. 3A and the actual test bed system is shown in FIG. 3B, with corresponding labels: A) infusion (in-flow) catheter(s); B) packed bed of modular scaffold; C) sponge foam of NPWT system; D) interface between packed bed and NPWT foam; E) negative pressure out-flow system that drives the direction and magnitude of fluid flow and evacuates excess fluid.

Porous media flow though the packed bed and the surface sponge was simulated using Darcy's law. Fluid volume fraction within the packed bed was estimated by averaging between random and hexagonal lattice estimations for spherical packing density and Carman-Kozeny relations were used to estimate hydraulic permeability. Simplified flow conditions through a cylindrical configuration were simulated and compared with analytical solutions to validate the model. Simulations were run for a range of particle size (200-400 μm). Predicted fluid velocity was highest in the immediate vicinity of the perfusion catheters with more uniformity of flow with increasing distance. Taken together, these preliminary data validate the approach of perfusing a packed bed of cell-seeded allograft microcarrier particles using a clinically relevant negative pressure wound system.

Example 2

Figure 4:
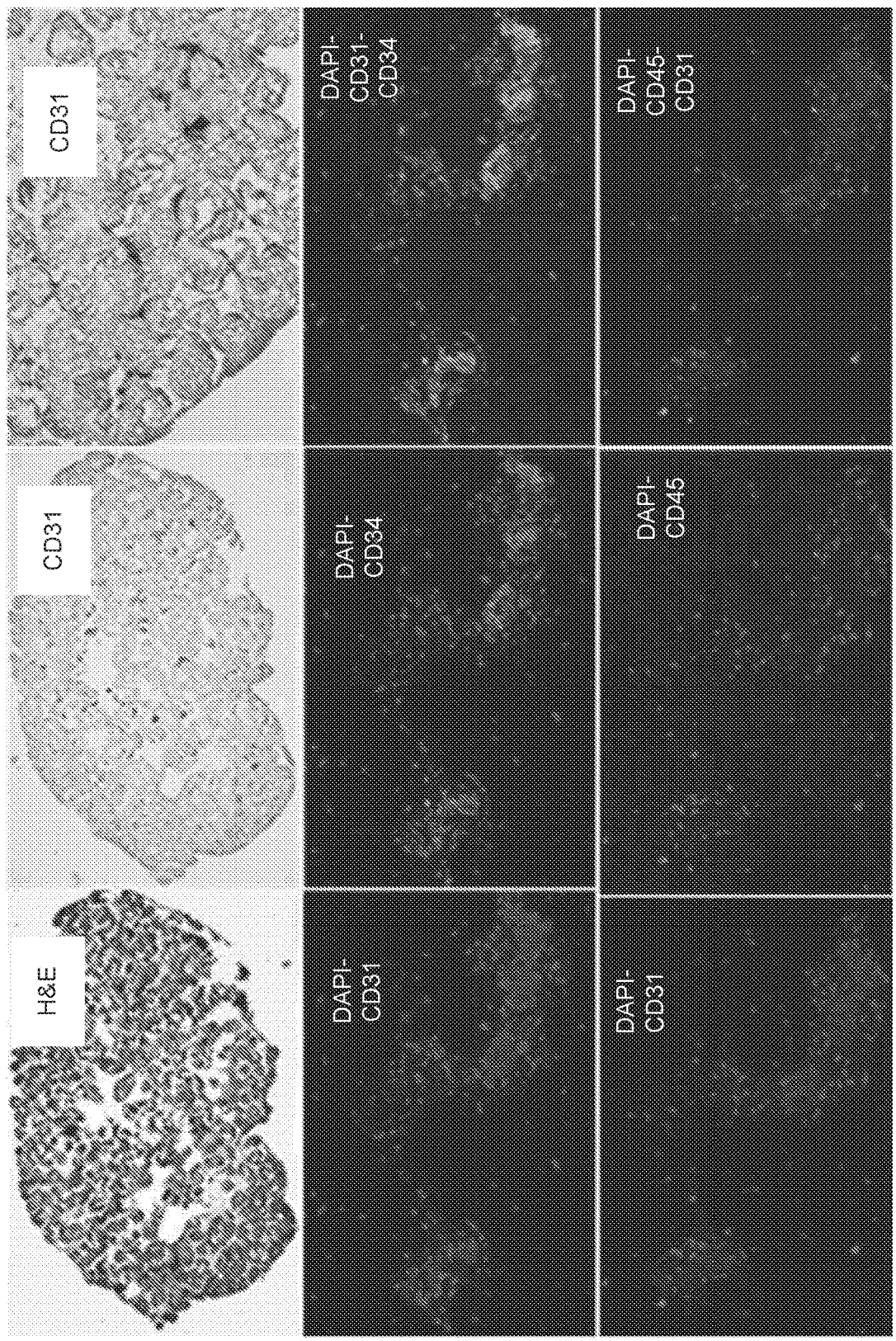
FIG. 4 is a series of images that illustrate cell phenotypes of human SVF cords grown in in a 2-D static bottom-up culture. The top row shows H&E staining (left) and CD31+ staining (darker spots, middle and right images). Middle row shows CD31 (left), CD34 (middle) and overlay of both (right). Bottom row shows CD31 (left), CD45 (middle) and overlay of both (right). The visible cords of cells are CD31+, CD45−, CD34+ supporting their identity as endothelial cells and endothelial progenitors, and not leukocytes.
Figure 5:
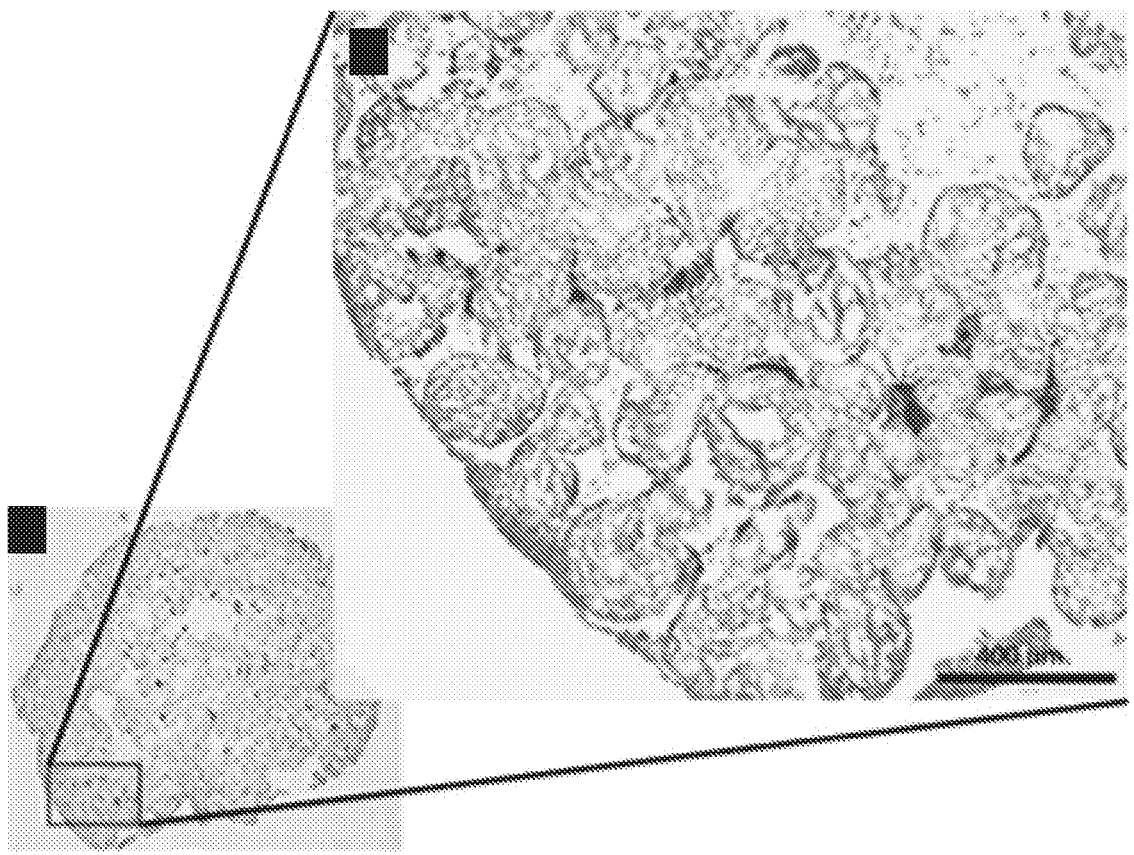
FIG. 5 is a larger view of the images form the top row CD31+ staining (middle and far right) of FIG. 4 with an enlarged view. The entire tissue construct is shown in the bottom left, and the call-out shows a cord of CD31+ cells (darker areas) that extend approximately 1.3 mm (scale bar+400 µm).

Cell Phenotype and Microvessel Cord Formation by Human SVF Cells Cultivated in Static 2-D Packed Bed Cultures After Seeding onto Gelatin Microspheres The present example demonstrated that human SVF cells seeded onto gelatin microspheres and maintained in static 2-D culture form cord-like vessel structures that are composed of CD31+, CD34+ and CD45− cells (e.g., endothelial cells) and span across multiple modular carriers (a distance of ~1300 μm). Described briefly, human SVF-seeded gelatin microspheres were statically cultured for 8 weeks in ultra-low adhesion plates, using DMEM+10% FBS. Constructs were paraffin embedded, sectioned, and stained using H&E and CD31 as shown in FIG. 4 (top row). Multi-label immunohistochemistry was also completed, utilizing combinations of CD31, CD34, and CD45 to identify cellular phenotypes (FIG. 4, middle and bottom row). In FIG. 4, the cellular phenotypes constituting this same cord are delineated: the vast majority of cells are CD45−, CD31+ and also CD34+, suggesting that they are composed of endothelial cells and endothelial progenitors, and not leukocytes which can cross react with CD31. As seen in FIG. 5 (a close-up view of the top middle and right images in FIG. 4), a CD31+ cord is visible spanning multiple microspheres and a distance of approximately 1300 μm. These results suggest that human SVF cells cultured as bottom-up modular scaffolds can self-assemble into vascular-like structures that span multiple units.

Example 3

Real-Time Isolation of Human SVF Cells Using a Novel Point-of-Care Device

The present example also demonstrated the routine isolation of stromal-vascular fraction (SVF) cells from human adipose tissue using a novel, disposable device for point-of-care therapies (The GID Group, Inc.). The device is currently in an FDA-approved pivotal trial for an orthopedic indication. Using this system, nearly 1 million viable nucleated cells can be isolated from each gram of adipose tissue processed with a viability of 82% of total nucleated cells. Flow cytometry studies demonstrate the reproducible presence of a variety of sub-populations within freshly isolated human SVF preparations including endothelial cells (~10%), endothelial progenitor cells (~10%), pericytes (up to ~40%), macrophages (~8%), and putative mesenchymal stem cells (up to ~30%)(submitted).

Adherence of Freshly Isolated Human SVF Cells to Modular Scaffolds

Figures 6A, 6B, 6C:
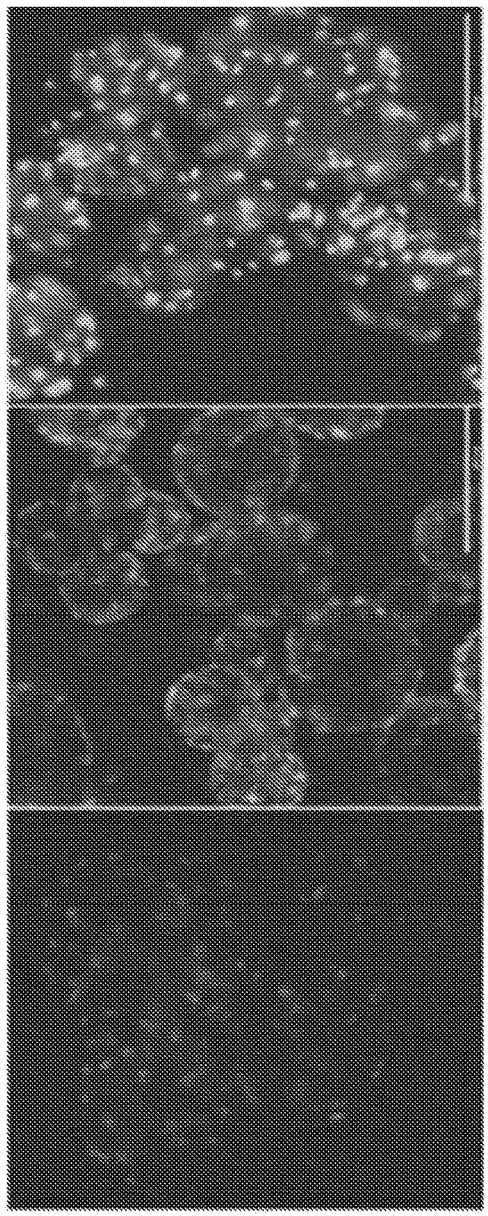
FIGS. 6A-D illustrate seeding efficiency of human adipose-derived cells onto gelatin microspheres. Culture-expanded ASCs attached better than freshly isolated SVF cells, but incubation beyond 4 hours did not appear to statistically enhance adherence of either cell type. Based on nuclear stain (6A) and viability stains (6B and 6C), cells appeared to attach with relative uniform dispersion.
Figure 6D:
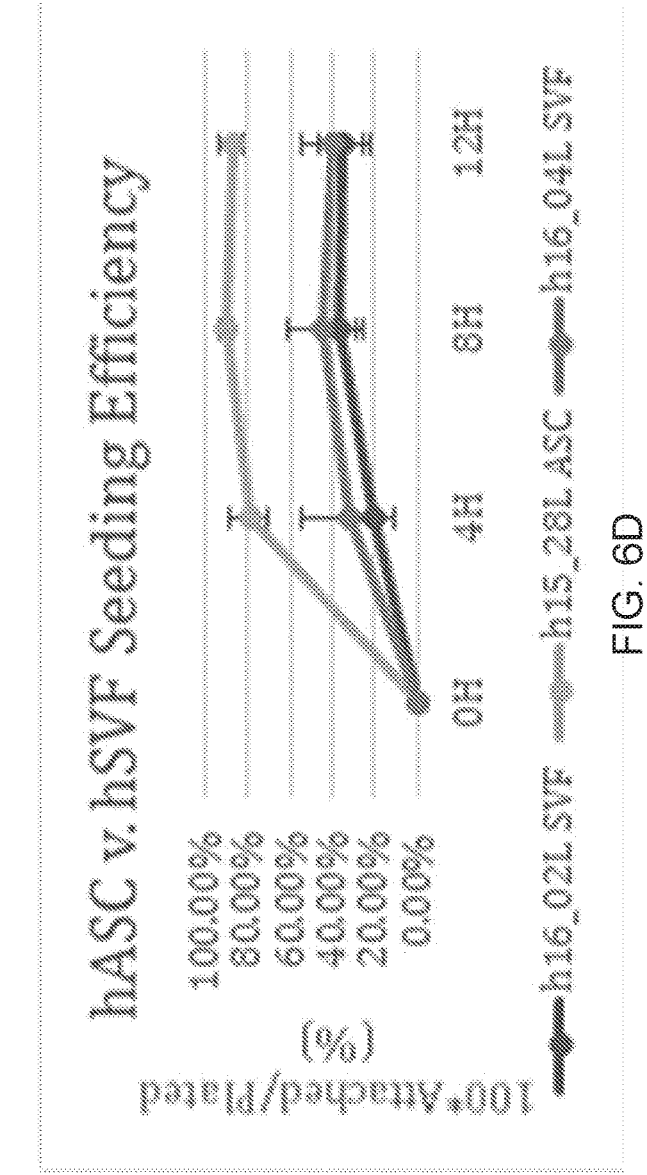

A potential limitation of the seeded modular scaffolding approach is the ability of freshly isolated SVF cells to attach to scaffolds in real time. Since freshly isolated SVF cells have been exposed to an enzymatic digestion, it was possible that cell membrane binding sites—such as integrin receptors—might not exist or function properly. Thus, the present example demonstrated the ability of SVF cells to adhere to modular scaffolding particles. There is a reported difference in the adherence of SVF cells and culture-expanded ASCs. For example, Frohlich et al. report 75% attachment of culture expanded ASCs to decellularized bone, whereas Jurgens et al. report only 10% attachment of SVF cells to poly(L-lactide-co-caprolactone) (PLCL) scaffolds (Frohlich, Grayson et al. 2010, Jurgens, Kroeze et al. 2011). In the present example seeding efficiencies of both human adipose-derived stromal cells (hASCs) and human SVF cells were calculated after seeding onto Cultispher® gelatin microspheres. Cells were counted at 4-hour intervals using a TC-10 automated cell-counter (Bio-Rad, Hercules, Calif.) and manually confirmed with a hemocytometer. Curves and statistics were generated using Excel and Prism, respectively.

hASC and hSVF seeding efficiencies were different, as demonstrated in FIGS. 6A-6D, with culture-expanded ASCs attached significantly better than freshly isolated SVF cells, but attachment did not change significantly for either cell type after 4-6 hours of incubation. Based on nuclear stain (6A blue color not shown) and viability stains (6B and 6C, green color not shown), cells appeared to attach with relative uniform dispersion. FIG. 6D is a graph illustrating the seeding efficiency of culture expanded ASC's vs. freshly isolated SVF cells.

Figures 7A, 7B, 7C:
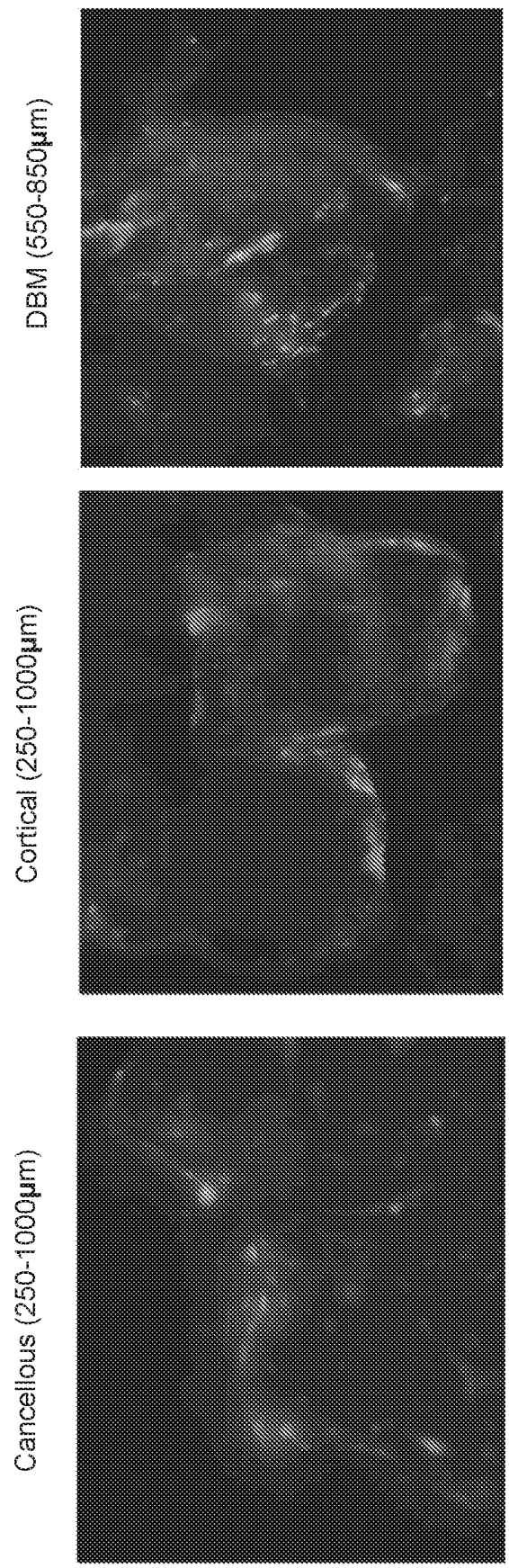
FIGS. 7A-C are images illustrating adherence of human adipose-derived cells to allogeneic scaffolds: cancellous, cortical, and demineralized bone matrix (DBM) particles. Particles were incubated in serum and then seeded with cells. DAPI staining of cell nuclei (blue, shows as darker fluorescent areas) and CytoGreen staining (green, shows as brighter fluorescent areas) of cytoplasm show robust cell attachment.

As further demonstration of seeding efficiencies, the results of the present example also demonstrated the feasibility of seeding human SVF cells onto clinically utilized allogeneic cortical-cancellous (CC) bone particles and demineralized bone matrix (DBM) particles. As shown in FIG. 7, cells were seeded onto cancellous (250-1000 μm), cortical (250-1000 μm), and DBM particles (500-850 μm). Particles were incubated in serum prior to seeding with the cells. Based on DAPI nuclear staining of cell nuclei (shows as darker fluorescent areas) and CytoGreen staining of cytoplasm (shows as brighter fluorescent areas), there is robust attachment of cells to these scaffold materials.

Example 4

Ex-Vivo Characterization of Fluid Flow Through Packed Beds of Modular Scaffolds

Figure 3A:
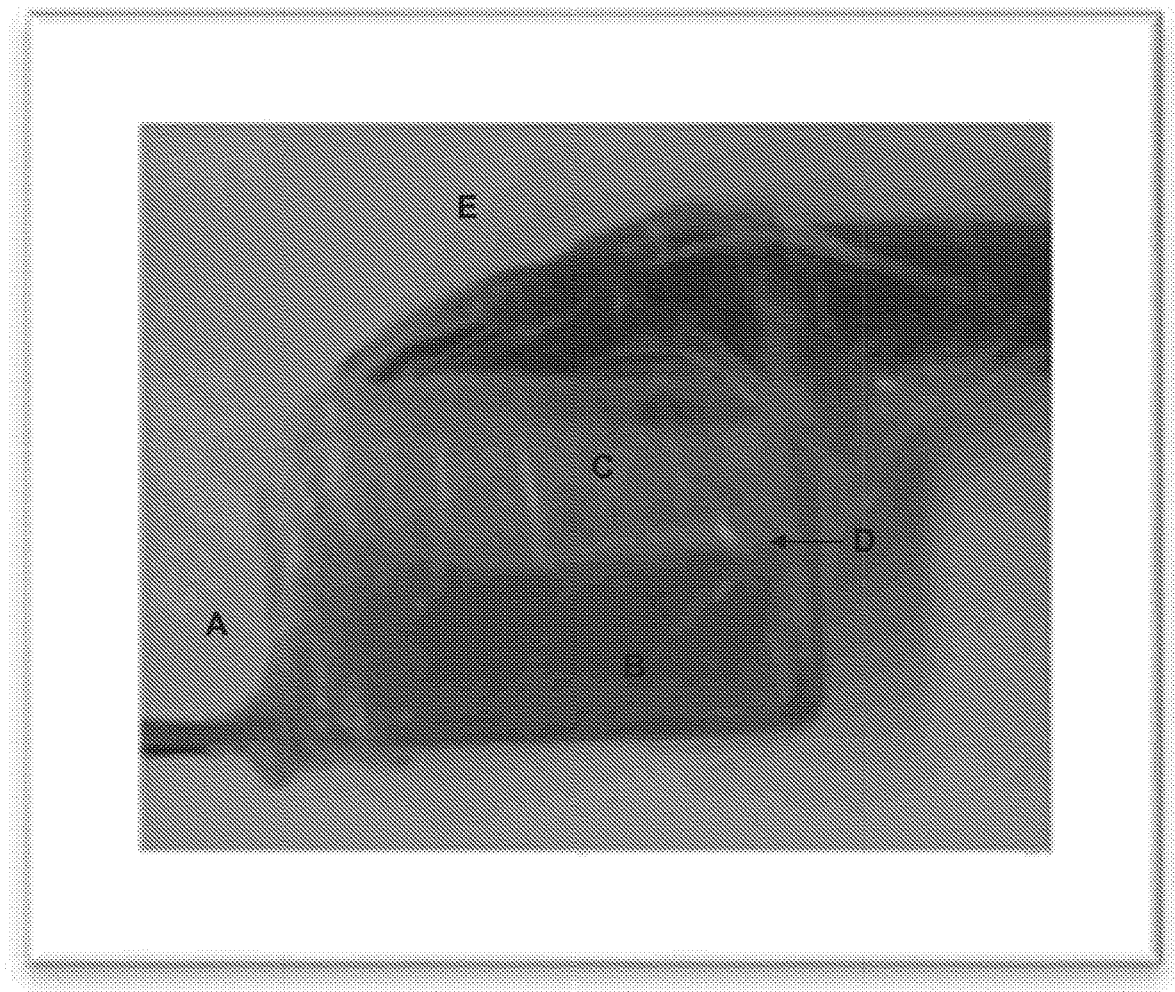
FIGS. 3A and 3B illustrate a customized ex-vivo embodiment of a system for evaluating the subatmospheric mediated perfusion of a packed bed assembly of modular scaffolding particles as used in Example 1.
Figure 3B:
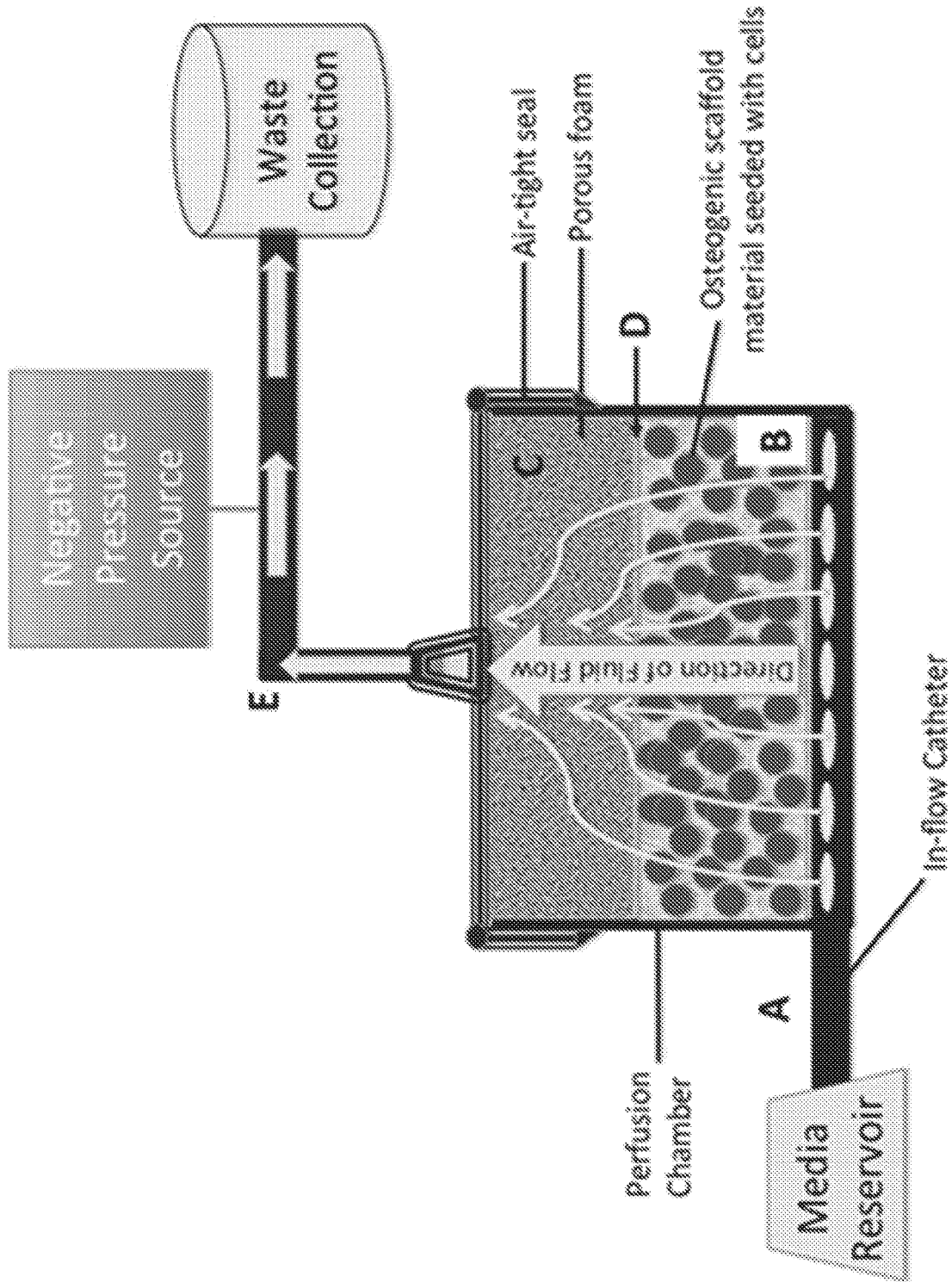

In additional studies, gelatin microsphere scaffolding particles (e.g., Cultispher®) of different sized (diameter) ranges will be placed into the packed bed chamber (B) of the model system shown in FIGS. 3A and B. Initial packed bed volumes of 6-8 ml will be used. Negative pressure will be applied using a controllable vacuum pump. As shown in the system of FIG. 2, a semipermeable seal and porous sponge material (C) will transmit subatmospheric pressure from the vacuum system to the packed bed assembly. Different variables are being tested by varying particle sizes, pressure amplitude and waveform, and the like. Particle sizes ranging from less than 200 microns, from 201-250 microns, 251-300 microns, 301 to 400 microns and greater than 400 microns are tested, as well as surface moficiation of the particles, such as with PBS (control) vs. 10% serum. Additionally, different pressures in physiologic ranges (e.g., values from 50 mmHg to 150 mmHG in increments of about 25 mmHg) are tested as well as various waveforms (e.g., since, square, continuous), and variations in the placement of the inflow and outflow conduits. Hydraulic permeability of the packed bed and surface sponge will also be independently confirmed by Dr. Sarntinoranont and team using a permeameter system. Since test chamber walls are transparent, uniformity of flows within the packed bed perfusion chamber will be visualized with particle or tracer tracking (e.g. Evans blue albumin) introduced through the inflow catheter. Sponge and particle bed compression will also be quantified by imaging and direct measurements. Changes in height will be used to estimate axial strain as a function of pressure within the chamber.

Example 5

In-Silica Modeling of Fluid Flow Through Packed Beds of Modular Scaffolds

In concert with the studies above, computational modeling efforts are being undertaken to determine the role of large-scale tissue perfusion on glucose transport and shear stresses within the packed bed. The goal of these models is to optimize flow and nutrient supply to MTFUs for different inlet and outlet conditions as well as delineate flow environment(s) that are permissive to cell attachment and growth, as well as vasculogenesis ((Ando and Yamamoto 2009, Ahsan and Nerem 2010, Cheng, Guan et al. 2013)). Perfusion flow through the packed bed will be optimized with respect to catheter placement, thickness and density of beds, and cell proliferation that changes the fluid volume fraction in the bed. Soft tissue biphasic models will provide the basis for analysis of deformation, flows, and nutrient distribution through and within the test chamber. Models will account for negative pressure effects such as nonlinear tissue consolidation behavior that potentially hinders perfusion, fluid shear stresses introduced with perfusion flow, and changes in nutrient uptake and perfusion with cell proliferation.

Figure 8A:
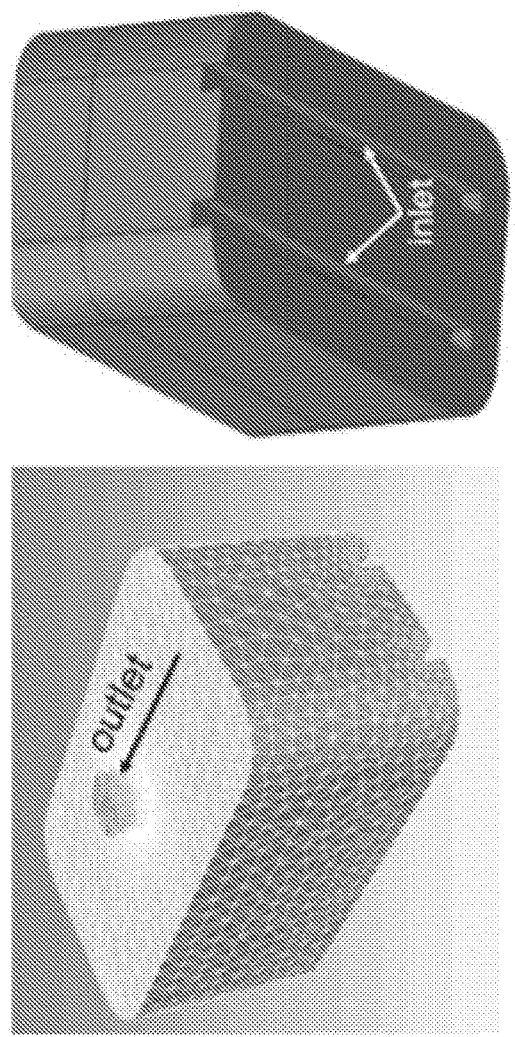
FIG. 8A illustrates a computation modeling approach.
Figure 8B:
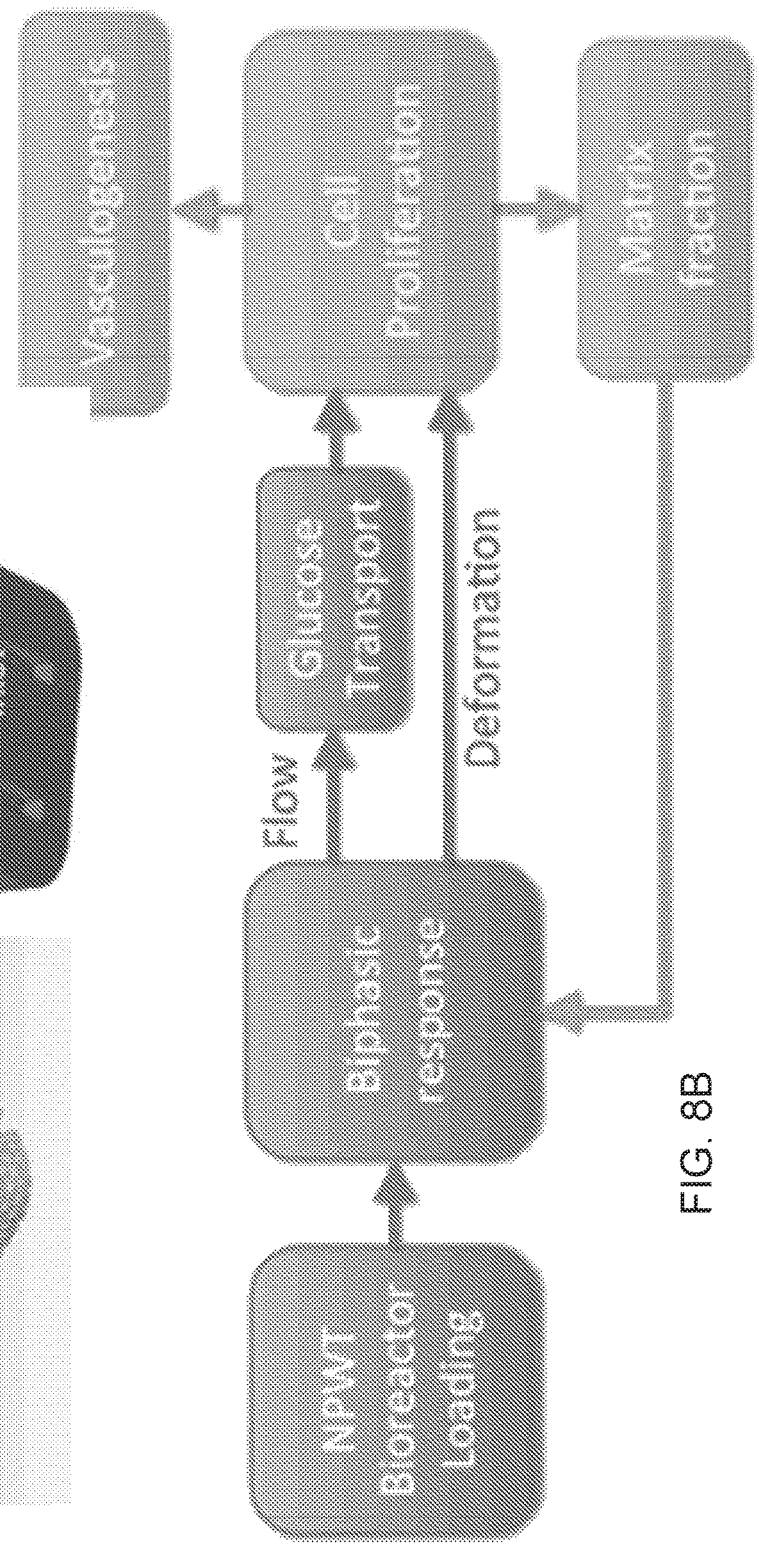
FIG. 8B is a schematic flow diagram of the computational modeling approach illustrating coupled factors in an embodiment of a computational model.

The packed bed assembly will be modeled with defined geometry similar to that shown in FIG. 8A. These computational models will capture ex-vivo conditions and will build upon previously developed interstitial transport models (Sarntinoranont, Chen et al. 2006, Chen and Sarntinoranont 2007, Pishko, Astary et al. 2011, Kim, Astary et al. 2012, Magdoom, Pishko et al, 2014) and transport analysis developed for perfusion bioreactors (Sengers, Oomens et al. 2004, Coletti, Macchietto et al. 2006, Chung, Chen et al. 2007, Sacco, Causin et al, 2011, Bandeiras, Completo et al. 2015). The packed bed of MTFUs will be represented by a porous media model consisting of two phases: a soft solid matrix and interconnected fluid space. To account for deformations, the solid matrix will be modeled as a hyperelastic, neo-Hookean material described by the strain energy density function, (Table 2, Eqn 1) where $\mu^s$, $\lambda^s$ are the Lamé's elastic constants of the solid matrix; $I_1$ is the first invariant of the left Cauchy-Green deformation tensor b; and j is the elastic volume ratio. Fluid perfusion through the bed will be described by Darcy's law or the Brinkman formula. To account for the effect of cell growth on transport within the packed bed, the Carman-Kozeny relation may be used to predict changes in permeability with cell proliferation and tissue compression (Bear 1972), (Table 2, Eqn 2) where $k_o$ is a reference permeability value. Darcy's law and the equations of conservation of mass and momentum govern the mechanical response of the biphasic material. Shear stress under perfusion can be estimated from the velocity field (Wang and Tarbell 2000) using the following relation, (Table 2, Eqn3) where T is the shear stress and $\mu$ is the dynamic viscosity. When shear stresses within the scaffold are too high, cells may detach. For these examples, a specified range (e.g., 0.1-15 dyne/cm$^2$) will be targeted to evaluate the effect of perfusion on vascular assembly (Yamamoto, Takahashi et al. 2003, Cheng, Guan et al. 2013, Obi, Yamamoto et al. 2014, Guyot, Luyten et al. 2015). Glucose uptake/consumption will also be considered to be a limiting factor for MTFU cell metabolism and proliferation. Mass transport will be modeled as advection and diffusion through the packed bed assembly. In addition, nutrient uptake by cells will be modeled by Michaelis-Menten kinetics (Coletti, Macchietto et al. 2006, Chung, Chen et al. 2007, Sengers, Please et al. 2008, Sacco, Causin et al. 2011). Changes in cell density, $\rho_{cell}$, may be modeled accounting for cell migration, proliferation and death (Table 2, Eqn 4). $D_{cell}$ accounts for cell migration due to random walks, $R_p$ and $R_d$ are cell proliferation and death rates respectively. Proliferation is based on glucose availability by Contois kinetics (Galban and Locke 1999, Galban and Locke 1999, Coletti, Macchietto et al. 2006) (Table 2, Eqn 5). $m_{max}$ is the maximum cell proliferation rate, $K_{eq}$ is the equilibrium coefficient of nutrient between solid and fluid phases, $K_s$ is the Contois saturation rate, $r_{sc}$ is the density of a cell, and $V_{sc}$ is a single cell volume. Increases in cell density will change permeability based on changes in fluid volume fractions (Eqn 2).

TABLE 2

| Equation 1 | $W = \frac{\mu^s}{2}(I_1 - 3) - \mu^s \ln J + \frac{\lambda^s}{2}(\ln J)^2$ |
| --- | --- |
| Equation 2 | $k = k_o \frac{\phi_f^3}{(1 - \phi_f)^2}$ |
| Equation 3 | $\tau = \frac{\mu|v|}{\sqrt{k}}$ |
| Equation 4 | $\frac{\partial \rho_{cell}}{\partial t} - D_{cell} \nabla^2 \cdot \rho_{cell} = (R_p - R_d)\rho_{cell}$ |
| Equation 5 | $R_p = \mu_{max} \frac{c_i}{K_{eq}^{-1} K_s \rho_{sc} V_{sc} \rho_{cell} + c_i}$ |

3D models will be developed using multiphysics software (COMSOL Inc., Burlington, Mass.). At the top surface of the NPWT foam, a boundary condition corresponding to the applied pressure waveform will be applied. Catheter pressure at the bottom of the bioreactor will be based on reservoir pressures. Displacements will be free in the z-direction. Glucose concentration at the perfusion outlet will match the test medium. Modeling parameters will initially be abstracted from literature, as well as from separate mechanical and transport testing as described above. In summary, computational models (FIG. 8A) will combine biphasic, transport, and cell growth equations to solve for fluid pressure, velocity, nutrient delivery, and shear stress, as well as tissue deformations within the bioreactor space under various conditions as listed above in Example 4.

Additionally, the impact of particle size, pressure amplitude, flow rates, and waveform on the self-assembly of neovessels in a perfused 3-dimensional packed bed assembly of cell-seeded scaffolds will also be evaluated. As a measure of mass transport/nutrient supply, cell metabolism and viability, glucose levels will be measured at the start of culture and over-time to determine the rate and amount of consumption, as previously described for 3-D oral mucosa constructs (Izumi, Song et al. 2004). Vascular network formation within consolidated constructs will be assessed using Image J software and previously described methods by quantifying the length of UAE-1+ or CD31+/CD45− cords, the number of nodes/branches and the number of particles that are bridged (Merfeld-Clauss, Gollahalli et al. 2010, Rioja, Tiruvannamalai Annamalai et al. 2016). Since dynamic culture (e.g. shear stress) may have different effects on cells relative to static conditions, these studies are not necessarily dependent on results from Example 1. However, we will analyze test variables (e.g., particles size, flow rate, pressure waveform) that produce shear forces in a range shown to be effective for stimulating vasculogenesis and tube formation (Yamamoto, Takahashi et al. 2003, Obi, Yamamoto et al. 2009, Ankeny, Ankeny et al. 2012, Cui, Zhang et al. 2012, Obi, Yamamoto et al, 2014) as well as the ex-vivo testing and in-silico modeling described above.

REFERENCES

Ahsan, T. and R. M. Nerem (2010). "Fluid shear stress promotes an endothelial-like phenotype during the early differentiation of embryonic stem cells." *Tissue Eng Part A* 16(11): 3547-3553.

Ando, J. and K. Yamamoto (2009). "Vascular mechanobiology: endothelial cell responses to fluid shear stress." *Circ J* 73(11): 1983-1992.

Amos et al., (2010) "Human Adiopose-Derived Stromal Cells Accelerate Diabetic Wound Healing: Impact of Cell Formulation and Delivery. Biofabrication and Amos et al., 2010, *Tissue Engineering*: Part A, 16(5): 1595-1606.

Ankeny, R. F., C. J. Ankeny, R. M. Nerem and H. Jo (2012). "Maturing EPCs into endothelial cells: may the force be with the EPCs: focus on "Fluid shear stress induces differentiation of circulating phenotype endothelial progenitor cells"." *Am J Physiol Cell Physiol* 303(6): C589-591.

Bandeiras, C., A. Completo and A. Ramos (2015). "Influence of the scaffold geometry on the spatial and temporal evolution of the mechanical properties of tissue-engineered cartilage: insights from a mathematical model." *Biomechanics and Modeling in Mechanobiology* 14(5): 1057-1070.

Bear, J. (1972). *Dynamics of fluids in porous materials*. New York, Elsevier.

Cao, Y. (2007). "Angiogenesis modulates adipogenesis and obesity." *J Clin Invest* 117(9): 2362-2368.

Chen, X. M., G. W. Astary, H. Sepulveda, T. H. Mareci and M. Sarntinoranont (2008). "Quantitative assessment of macromolecular concentration during direct infusion into an agarose hydrogel phantom using contrast-enhanced MRI." *Magnetic Resonance Imaging* 26(10): 1433-1441.

Chen, X. M. and M. Sarntinoranont (2007). "Biphasic finite element model of solute transport for direct infusion into nervous tissue," *Annals of Biomedical Engineering* 35(12): 2145-2158.

Cheng, M., X. Guan, H. Li, X. Cui, X. Zhang, X. Li, X. Jing, H. Wu and E. Avsar (2013). "Shear stress regulates late EPC differentiation via mechanosensitive molecule-mediated cytoskeletal rearrangement." *PLoS One* 8(7): e67675.

Chung, C. A., C. W. Chen, C. P. Chen and C. S. Tseng (2007). "Enhancement of cell growth in tissue-engineering constructs under direct perfusion: Modeling and simulation." *Biotechnology and Bioengineering* 97(6): 1603-1616.

Coletti, F., S. Macchietto and N. Elvassore (2006). "Mathematical modeling of three-dimensional cell cultures in perfusion bioreactors." *Industrial & Engineering Chemistry Research* 45(24): 8158-8169.

Cook, C. A., K. C. Hahn, J. B. Morrissette-McAlmon and W. L. Grayson (2015). "Oxygen delivery from hyperbarically loaded microtanks extends cell viability in anoxic environments." *Biomaterials* 52: 376-384.

Cui, X., X. Zhang, X. Guan, H. Li, X. Li, H. Lu and M. Cheng (2012). "Shear stress augments the endothelial cell differentiation marker expression in late EPCs by upregulating integrins." *Biochem Biophys Res Commun* 425(2): 419-425.

Davis, K. E., et al., (2016) "The fluid dynamics of simultaneous irrigation with negative pressue wound therapy," *International Wound Journal* 13:469-474.

Dullien, F. A. L. (1992) "Porous Media: Fluid Transport and Pore Structure", $2^{nd}$, Ed., Academic Press.

Frohlich, M., W. L. Grayson, D. Marolt, J. M. Gimble, N. Kregar-Velikonja and G. Vunjak-Novakovic (2010). "Bone grafts engineered from human adipose-derived stem cells in perfusion bioreactor culture." *Tissue Eng Part A* 16(1): 179-189.

Fukumura, D., A. Ushiyama, D. G. Duda, L. Xu, J. Tam, V. Krishna, K. Chatterjee, I. Garkavtsev and R. K. Jain (2003). "Paracrine regulation of angiogenesis and adipocyte differentiation during in vivo adipogenesis." *Circ Res* 93(9): e88-97.

Galban, C. J. and B. R. Locke (1999). "Analysis of cell growth kinetics and substrate diffusion in a polymer scaffold." *Biotechnol Bioeng* 65(2): 121-132.

Galban, C. J. and B. R. Locke (1999). "Effects of spatial variation of cells and nutrient and product concentrations coupled with product inhibition on cell growth in a polymer scaffold," *Biotechnol Bioeng* 64(6): 633-643.

Guyot, Y., F. P. Luyten, J. Schrooten, I. Papantoniou and L. Geris (2015). "A three-dimensional computational fluid dynamics model of shear stress distribution during neotissue growth in a perfusion bioreactor," *Biotechnol Bioeng*.

Huang, C., T. Leavitt, L. R. Bayer and D. P. Orgill (2014). "Effect of negative pressure wound therapy on wound healing." *Curr Probl Surg* 51(7): 301-331.

Izumi, K., J. Song and S. E. Feinberg (2004). "Development of a tissue-engineered human oral mucosa: from the bench to the bed side." *Cells Tissues Organs* 176(1-3): 134-152.

Jabalee, J. and T. A. Franz-Odendaal (2015). "Vascular endothelial growth factor signaling affects both angiogenesis and osteogenesis during the development of scleral ossicles." *Dev Biol* 406(1): 52-62.

Jandial, R., M. Y. Chen and J. Ciacci (2011). "HIF-1alpha potentiates mesenchymal stem cell mediated osteogenesis by coupling to angiogenesis." *Neurosurgery* 69(4): N13-14.

Jurgens, W. J., R. J. Kroeze, R. A. Bank, M. J. Ritt and M. N. Helder (2011), "Rapid attachment of adipose stromal cells on resorbable polymeric scaffolds facilitates the one-step surgical procedure for cartilage and bone tissue engineering purposes." *J Orthop Res* 29(6): 853-860, Kapur, S. K., et al., (2012), "Human adipose stem cells maintain proliferative, synthetic, and multopotential properties when suspension cultured as self-assembling spheroids." *Biofabrication* 4. 025004.

Kim, J. H., G. W. Astary, S. Kantorovich, T. H. Mareci, P. R. Carney and M. Sarntinoranont (2012). "Voxelized Computational Model for Convection-Enhanced Delivery in the Rat Ventral Hippocampus: Comparison with In Vivo MR Experimental Studies." *Annals of Biomedical Engineering* 40(9): 2043-2058.

Kusumbe, A. P., S. K. Ramasamy and R. H. Adams (2014). "Coupling of angiogenesis and osteogenesis by a specific vessel subtype in bone." *Nature* 507(7492): 323-328.

Magdoom, K. N., G. L. Pishko, L. Rice, C. Pampo, D. W. Siemann and M. Sarntinoranont (2014). "MRI-Based Computational Model of Heterogeneous Tracer Transport following Local Infusion into a Mouse Hind Limb Tumor." *Plos One* 9(3).

McClung, J. M., J. L. Reinardy, S. B. Mueller, T. J. McCord, C. D. Kontos, D. A. Brown, S. N. Hussain, C. A. Schmidt, T. E. Ryan and T. D. Green (2015). "Muscle cell derived angiopoietin-1 contributes to both myogenesis and angiogenesis in the ischemic environment." *Front Physiol* 6: 161.

Merfeld-Clauss, S., N. Gollahalli, K. L. March and D. O. Traktuev (2010). "Adipose tissue progenitor cells directly interact with endothelial cells to induce vascular network formation." *Tissue Eng Part A* 16(9): 2953-2966.

Obi, S., K. Yamamoto and J. Ando (2014). "Effects of shear stress on endothelial progenitor cells." *J Biomed Nanotechnol* 10(10): 2586-2597.

Obi, S., K. Yamamoto, N. Shimizu, S. Kumagaya, T. Masumura, T. Sokabe, T. Asahara and J. Ando (2009). "Fluid shear stress induces arterial differentiation of endothelial progenitor cells." *J Appl Physiol* (1985) 106(1): 203-211.

Pishko, G. L., G. W. Astary, T. H. Mareci and M. Sarntinoranont (2011). "Sensitivity Analysis of an Image-Based Solid Tumor Computational Model with Heterogeneous Vasculature and Porosity." *Annals of Biomedical Engineering* 39(9): 2360-2373.

Pishko, G. L., S. J. Lee, P. Wanakule and M. Sarntinoranont (2007). "Hydraulic permeability of a hydrogel-based contact lens membrane for low flow rates." *Journal of Applied Polymer Science* 104(6): 3730-3735.

Ramasamy, S. K., A. P. Kusumbe, L. Wang and R. H. Adams (2014). "Endothelial Notch activity promotes angiogenesis and osteogenesis in bone." *Nature* 507(7492): 376-380.

Renault, M. A., S. Vandierdonck, C. Chapouly, Y. Yu, G. Qin, A. Metras, T. Couffinhal, D. W. Losordo, Q. Yao, A. Reynaud, B. Jaspard-Vinassa, I. Belloc, C. Desgranges and A. P. Gadeau (2013). "Gli3 regulation of myogenesis is necessary for ischemia-induced angiogenesis." *Circ Res* 113(10): 1148-1158.

Rioja, A. Y., R. Tiruvannamalai Annamalai, S. Paris, A. J. Putnam and J. P. Stegemann (2016). "Endothelial sprouting and network formation in collagen- and fibrin-based modular microbeads," *Acta Biomater* 29: 33-41.

Ruan, L., B. Wang, Q. ZhuGe and K. Jin (2015). "Coupling of neurogenesis and angiogenesis after ischemic stroke." *Brain Res* 1623: 166-173.

Sacco, R., P. Causin, P. Zunino and M. T. Raimondi (2011). "A multiphysics/multiscale 2D numerical simulation of scaffold-based cartilage regeneration under interstitial perfusion in a bioreactor." *Biomechanics and Modeling in Mechanobiology* 10(4): 577-589.

Sarntinoranont, M., X. M. Chen, J. B. Zhao and T. H. Mareci (2006). "Computational model of interstitial transport in the spinal cord using diffusion tensor imaging." *Annals of Biomedical Engineering* 34(8): 1304-1321.

Sengers, B. G., C. W. J. Oomens and F. P. T. Baaijens (2004). "An integrated finite-element approach to mechanics, transport and biosynthesis in tissue engineering." *Journal of Biomechanical Engineering-Transactions of the Asme* 126(1): 82-91.

Sengers, B. G., C. P. Please, M. Taylor and R. O. C. Oreffo (2008). "A computational model relating 2D cell spreading to 3D scaffold colonization for skeletal tissue regeneration." *Calcified Tissue International* 83(1): 14-14.

Shu, Y., B. Xiao, Q. Wu, T. Liu, Y. Du, H. Tang, S. Chen, L. Feng, L. Long and Y. Li (2016). "The Ephrin-A5/EphA4 Interaction Modulates Neurogenesis and Angiogenesis by the p-Akt and p-ERK Pathways in a Mouse Model of TLE." *Mol Neurobiol* 53(1): 561-576.

Tiruvannamalai-Annamalai, Ramkumar; Randall Armant, David; W. T. Matthew, Howard (2014): *A Glycosaminoglycan Based, Modular Tissue Scaffold System for Rapid Assembly of Perfusable, High Cell Density, Engineered Tissues*, PLoS ONE 9(1):e84287

Wang, S. and J. M. Tarbell (2000). "Effect of fluid flow on smooth muscle cells in a 3-dimensional collagen gel model." *Arteriosclerosis Thrombosis and Vascular Biology* 20(10): 2220-2225.

Yamamoto, K., T. Takahashi, T. Asahara, N. Ohura, T. Sokabe, A. Kamiya and J. Ando (2003). "Proliferation, differentiation, and tube formation by endothelial progenitor cells in response to shear stress." *J Appl Physiol* (1985) 95(5): 2081-2088.

The invention claimed is:

1. An in situ, in vivo tissue generation and repair system comprising:
   a plurality of modular tissue forming units (MTFUs) packed in a tissue defect, the plurality of MTFUs comprising: a plurality of biocompatible scaffolding particles seeded with a plurality of exogenous cells capable of forming at least one tissue type needed to repair a tissue defect, wherein the cells are coupled to the scaffolding particles;
   a perfusion fluid delivery conduit placed in the tissue defect with the MTFUs and adapted to deliver media to the tissue defect packed with the MTFUs; and
   a negative pressure wound therapy (NPWT) system comprising a negative pressure wound dressing (NPWD) coupled to a subatmospheric pressure (SAP) device, the NPWT system adapted to interface with the tissue defect packed with MTFUs so as to pull media through void spaces between the MTFUs packed within the tissue defect to perfuse the cells coupled to the MTFUs with the media and to evacuate excess media or other fluid.

2. The tissue generation system of claim 1, wherein the biocompatible scaffolding particles have an average diameter of about 25 to 1000 µm.

3. The tissue generation system of claim 1, wherein the biocompatible scaffolding particles are selected from the group consisting of: cortical-cancellous (CC) bone particles, demineralized bone matrix (DBM) particles, and gelatin microspheres.

4. The tissue generation system of claim 1, wherein the biocompatible scaffolding particles are seeded with cells at a seeding density of about 100,000 to 10 million cells/mg.

5. The tissue generation system of claim 1, wherein the cells are human stem cells or human progenitor cells, and wherein the cells are autologous or allogenic.

6. The tissue generation system of claim 1, wherein the cells are human adipose derived stem cells (ADSCs) or adipose derived stromal vascular fraction (SVF) cells.

7. The tissue generation system of claim 1, wherein the perfusion fluid comprises growth media.

8. The tissue generation system of claim 1, further comprising:
   a media reservoir coupled to the perfusion fluid delivery conduit to provide media for delivery to the tissue defect, and
   a pump coupled to one or more of the media reservoir or the perfusion fluid delivery conduit to initiate flow of fluid from the media reservoir through the perfusion fluid delivery conduit to the tissue defect.

9. The tissue generation system of claim 1, wherein the NPWD comprises a porous foam material.

10. The tissue generation system of claim 1, wherein the SAP device comprises a negative pressure source coupled to an out-flow conduit.

11. A method of in-situ, in vivo tissue regeneration and repair, the method comprising:

providing a plurality of modular tissue forming units (MTFUs), the MTFUs comprising: a plurality of biocompatible scaffolding particles seeded with a plurality of exogenous cells capable of forming at least one tissue type needed to repair a tissue defect;

packing a tissue defect with the plurality of MTFUs such that void spaces exist between the MTFUs;

providing a perfusion fluid delivery conduit having one or more fluid delivery outlets in the packed tissue defect to deliver a fluid to the MTFU-packed tissue defect;

applying a negative pressure wound therapy (NPWT) system to the packed tissue defect, the NPWT system comprising a negative pressure wound dressing (NPWD) coupled to a subatmospheric pressure (SAP) device, the NPWT system adapted to interface with the MTFU-packed tissue defect, such that the NPWD seals the MTFU-packed tissue defect; and creating a pressure gradient with the SAP device to direct the flow of fluid(s) from the perfusion fluid delivery conduit through the void spaces between the MTFUs to an exit conduit.

12. The method of claim 11, wherein the perfusion delivery conduit is placed such that at least one of the fluid delivery outlets is located inferior to at least a portion of the MTFUs.

13. The method of claim 11, wherein the biocompatible scaffolding particles are selected from the group consisting of cortical-cancellous (CC) bone particles, demineralized bone matrix (DBM) particles, and gelatin microspheres.

14. The method of claim 11, wherein the cells are human cells capable of differentiating into endothelial cells and wherein the perfusion fluid comprises growth media.

15. The method of claim 11, wherein the perfusion fluid delivery conduit is coupled to a media reservoir to provide media for delivery to the tissue defect.

16. The method of claim 11, wherein the SAP device comprises a negative pressure source coupled to a negative pressure out-flow conduit.

17. The method of claim 11, wherein at least a portion of the cells differentiate into endothelial cells and form vessels among the scaffolding particles.

18. The method of claim 11, wherein the fluid is continuously perfused through the tissue defect, and wherein the flow rate is a function of a flow of the fluid from a pump coupled to the perfusion catheter and the subatmosphereic pressure generated by the SAP device and NPWD.

19. The method of claim 11, wherein the fluid is intermittently perfused through the tissue defect such that the tissue defect is infused with fluid, which is removed via the NPWT system after a time period of about 30 min to 24 hours.

20. The method of claim 11, further comprising, prior to packing the tissue defect with MTFUs, imaging the tissue defect with a 3D imaging device to produce 3D imaging data, calculating the volume and shape of the tissue defect based on the 3D imaging data; optimizing the placement of the perfusion fluid delivery conduit and the packing density of the MTFU's based on the calculated volume and shape of the tissue defect.

* * * * *

UNITED STATES PATENT AND TRADEMARK OFFICE
CERTIFICATE OF CORRECTION

| | | |
|---|---|---|
| PATENT NO. | : 11,577,062 B2 | |
| APPLICATION NO. | : 16/604900 | |
| DATED | : February 14, 2023 | |
| INVENTOR(S) | : Adam J. Katz | |

It is certified that error appears in the above-identified patent and that said Letters Patent is hereby corrected as shown below:

In the Specification

Column 1, Line 16, under Paragraph Titled "STATEMENT REGARDING FEDERALLY SPONSORED RESEARCH OR DEVELOPMENT" should read "This invention was made with government support under Grant Number W81XWH-13-2-0054, awarded by the United States Army. The government has certain rights in the invention."

Signed and Sealed this
Fifteenth Day of October, 2024

Katherine Kelly Vidal
*Director of the United States Patent and Trademark Office*